US008865075B2

(12) United States Patent
Guzman

(10) Patent No.: US 8,865,075 B2
(45) Date of Patent: Oct. 21, 2014

(54) MULTI-TASK IMMUNOAFFINITY DEVICE SECURED TO A PERIPHERAL BOX AND INTEGRATED TO A CAPILLARY ELECTROPHORESIS APPARATUS

(75) Inventor: Norberto A. Guzman, East Brunswick, NJ (US)

(73) Assignee: Princeton Biochemicals, Inc., Princeton, NJ (US)

( * ) Notice: Subject to any disclaimer, the term of this patent is extended or adjusted under 35 U.S.C. 154(b) by 125 days.

(21) Appl. No.: 13/284,087

(22) Filed: Oct. 28, 2011

(65) Prior Publication Data

US 2012/0103816 A1      May 3, 2012

Related U.S. Application Data

(60) Provisional application No. 61/408,689, filed on Nov. 1, 2010.

(51) Int. Cl.
*G01N 21/00*      (2006.01)
*G01N 33/543*     (2006.01)
(Continued)

(52) U.S. Cl.
CPC ... *G01N 27/44743* (2013.01); *B01L 2300/0809* (2013.01); *G01N 33/543* (2013.01); *B01L 2200/028* (2013.01); *B01L 3/50* (2013.01);
(Continued)

(58) Field of Classification Search
CPC ......... G01N 27/447–27/44782; G01N 33/543; G01N 33/53; G01N 33/5302; G01N 33/54313; G01N 33/54353; G01N 30/466; G01N 30/74; G01N 2030/326; B01L 9/527; B01L 3/50–3/502784; B01L 2200/026–2200/028; B01L 2200/0668; B01L 2200/0673; B01L 2200/10; B01L 2300/021; B01L 2300/0627; B01L 2300/0809; B01L 2300/0861; B01L 2300/0867; B01L 2300/087; B01L 2300/0877; B01L 2400/0415–2400/0436; B01L 2400/06–2400/082
USPC .......... 424/551–566; 422/50, 68.1, 81, 82.01, 422/82.05, 82.07, 82.08; 435/5, 7.1
See application file for complete search history.

(56) References Cited

U.S. PATENT DOCUMENTS 5,202,010 A    4/1993  Guzman
5,741,639 A    4/1998  Ensing et al.
(Continued)

OTHER PUBLICATIONS

Ramsey et al., "High-Efficiency, Two-Dimensional Separations of Protein Digests on Microfluidic Devices" Anal. Chem. 75:3758-3764 (2003).

(Continued)

*Primary Examiner* — Melanie Y Brown
*Assistant Examiner* — Erik B Crawford
(74) *Attorney, Agent, or Firm* — Porzio, Bromberg & Newman, P.C.

(57) ABSTRACT

The present invention relates to an immunoaffinity device for capturing one or more analytes present at high or low concentrations in simple or complex matrices. The device is designed as a modular, multi-task immunoaffinity device secured to a peripheral box and connected to capillary electrophoresis or liquid chromatography for the isolation, enrichment, separation and identification of polymeric macromolecules, primarily protein biomarkers. In one embodiment, two devices are coupled in-tandem to perform separately and sequentially microreactions and concentrations of proteins. In this embodiment, biological samples containing proteins can be subjected to proteolytic processing in the first device, and the resulting peptides subjected to selective purification and concentration in the second device.

58 Claims, 8 Drawing Sheets

(51) Int. Cl.
*B01L 3/00* (2006.01)
*G01N 33/53* (2006.01)
*G01N 27/447* (2006.01)
*B01L 9/00* (2006.01)
*G01N 30/74* (2006.01)
*G01N 30/46* (2006.01)
*G01N 30/32* (2006.01)

(52) U.S. Cl.
CPC ........... *G01N 33/53* (2013.01); *B01L 2200/027* (2013.01); *B01L 2300/0861* (2013.01); *B01L 2400/0415* (2013.01); *B01L 2200/0668* (2013.01); *B01L 3/502* (2013.01); *B01L 2400/06* (2013.01); *G01N 2030/326* (2013.01); *B01L 9/527* (2013.01); *B01L 2200/10* (2013.01); *G01N 30/74* (2013.01); *G01N 30/466* (2013.01); *B01L 2400/082* (2013.01); *B01L 2300/021* (2013.01); *B01L 2300/0627* (2013.01); *B01L 2200/0673* (2013.01); *B01L 3/5025* (2013.01); *B01L 2200/026* (2013.01)
USPC ........... 422/82.01; 422/50; 422/68.1; 422/81; 422/82.05; 422/82.07; 422/82.08; 435/5; 435/7.1

(56) References Cited

U.S. PATENT DOCUMENTS

| | | | |
|---|---|---|---|
| 5,800,692 A | 9/1998 | Naylor et al. | |
| 6,406,604 B1 | 6/2002 | Guzman | |
| 6,828,116 B1 * | 12/2004 | Hamilton et al. | 435/23 |
| 7,329,388 B2 | 2/2008 | Guzman | |
| 7,407,568 B1 | 8/2008 | Malik et al. | |
| 7,736,480 B2 | 6/2010 | Guzman | |
| 7,811,436 B2 | 10/2010 | Guzman | |
| 7,828,948 B1 | 11/2010 | Hatch et al. | |
| 7,959,861 B2 | 6/2011 | Lopez et al. | |
| 8,007,724 B2 | 8/2011 | Guzman | |
| 8,007,725 B2 | 8/2011 | Guzman | |
| 8,030,092 B2 | 10/2011 | Guzman | |
| 2007/0031283 A1 * | 2/2007 | Davis et al. | 422/58 |
| 2008/0115599 A1 * | 5/2008 | Masters et al. | 73/866 |
| 2011/0105354 A1 * | 5/2011 | Glezer et al. | 506/9 |

OTHER PUBLICATIONS

Guzman, N. A. "Improved solid-phase microextraction device for use in on-line immunoaffinity capillary electrophoresis" Electrophoresis 24:3718-3727 (2003).

Li et al. "Integration of Isoelectric Focusing with Parallel Sodium Dodecyl Sulfate Gel Electrophoresis for Multidimensional Protein Separations in a Plastic Microfludic Network" Anal. Chem. 76:742-748 (2004).

Guzman, N.A. "Immunoaffinity capillary electrophoresis applications of clinical and pharmaceutical relevance" Anal Bioanal Chem 378:37-39 (2004).

Ye et al., "On-line protein digestion and peptide mapping by capillary electrophoresis with post-column labeling for laser-induced fluorescence detection" Electrophoresis 25:1319-1326 (2004).

Renzi et al., "Hand-Held Microanalytical Instrument for Chip-Based Electrophoretic Separations of Proteins" Anal. Chem. 77:435-441 (2005).

Guzman et al., "Proteonnics Studies—This 2-D separation technique can complement MS-based proteomics methods" Analytical Chemistry 61-67 (2005).

Kartalov et al., "High-throughput multi-antigen microfluidic fluorescence immunoassays" BioTechniques 40 (1):85-90 (2006).

Mallik et al., "Affinity monolith chromatography" J. Sep. Sci. 29:1686-1704 (2006).

Nagrath et al."Isolation of rare circulating tumour cells in cancer patients by microchip technology" Nature 450 (20/27) 1235-1241 (2007).

Khurana et al. "Preconcentration, Separation, and Indirect Detection of Nonfluorescent Analytes Using Fluorescent Mobility Markers" Anal. Chem. 80:279-286 (2008).

Guzman et al., "Immunoaffinity capillary electrophoresis as a powerful strategy for the quantification of low-abundance biomarkers, drugs, and metabolites in biological matrices" Electrophoresis 29:3259-3278 (2008).

Chen et al. "Magnetic Beads Based Immunoaffinity Capillary Electrophoresis of Total Serum IgE with Laser-Induced Fluorescence Detection" Anal. Chem. 80:9583-9588 (2008).

Phillips et al., "Enrichment of Cancer Cells Using Aptamers Immobilized on a Microfluidic Channel" Anal. Chem. 81:1033-1039 (2009).

Yuen et al. "Multidimensional modular microfluidic system" Lab Chip, 9:3303-3305 (2009).

Phillips et al., "Immunoaffinity Techniques in Analysis" J Chromatogr B Analyt Technol Biomed Life Sci. 878(2):113 (2010).

Moser et al. "Immunoaffinity chromatography: an introduction to applications and recent developments" Bioanalysis. 2(4)769-790 (2010).

Dharmasiri et al. "Microsystems for the Capture of Low-Abundance Cells" Annu. Rev. Anal. Chem. 3:409-31 (2010).

Parker et al., "Mass-spectrometry-based clinical proteomics—a review and prospective" Analyst, 135:1830-1838 (2010).

Guzman et al., "Immunoaffinity capillary electrophoresis: A new versatile tool for determining protein biomarkers in inflammatory processes" Electrophoresis 32:1565-1578 (2011).

Hua et al., "On-chip solid phase extraction and enzyme digestion using cationic PolyE-323 coatings and porous polymer monoliths coupled to electrospray mass spectrometry" Journal of Chromatography A, 1218:4039-4044 (2011).

Wang et al., "Effect of Surface Nanotopography on Immunoaffinity Cell Capture in Microfluidic Devices" Langmuir 27:11229-11237 (2011).

Whiteaker et al., "Peptide Immunoaffinity Enrichment Coupled with Mass Spectrometry for Peptide and Protein Quantification" Clin Lab Med 31:385-396 (2011).

* cited by examiner

MULTI-TASK IMMUNOAFFINITY DEVICE SECURED TO A PERIPHERAL BOX AND INTEGRATED TO A CAPILLARY ELECTROPHORESIS APPARATUS

CROSS REFERENCE TO RELATED APPLICATION

This application claims the benefits of U.S. Provisional Patent Application No. 61/408,689 filed on Nov. 1, 2010, the entirely of which is hereby incorporated by reference into this application.

BACKGROUND OF THE INVENTION

1. Field of the Invention

The present invention relates generally to the analysis of chemical and biological materials and, more particularly, to a modular, multi-task immunoaffinity device secured to a peripheral box and connected to capillary electrophoresis for the isolation, enrichment, separation, identification and characterization of protein biomarkers and a large diversity of analytes found at a wide range of concentrations in simple and complex mixtures. Furthermore, when two or more devices are connected in tandem to perform microreactions in one and concentrations in the other, a powerful tool is created to generate peptide cleavage of proteins and further purification and concentration of one or more resulting peptides.

2. Description of Related Art

Technology in the twenty-first century is shrinking at a rather rapid rate. As a result, more and more advancements are taking place at the cellular, molecular and atomic level. With scientific understanding growing, it is becoming possible to engineer the smallest devices and applications to help in a variety of fields. One of the fields that is likely to benefit greatly from miniaturization is life science. Microfabrication techniques have improved rapidly over the last decade, stimulated primarily by advancements in the microprocessor industry. Small, fast and easy-to-operate devices or instruments are needed to reduce the inherent cost and inefficiencies associated with healthcare testing in clinical laboratories. Miniaturized devices are ideally suited for using small volumes of samples and reagents, performing chemical and biochemical reactions in short periods of time, under controllable microenvironments, cost effective, environmental friendly and portables. Unfortunately, as the power of fabrication allows the manufacturing of small devices with feature sizes as small as a few microns, it becomes inevitable that the requirement of sample volumes also becomes small. As a consequence, very small sample volumes compromise the issue of sensitivity making difficult the process of isolation and quantification of analytes of interest and/or their respective modified and/or altered corresponding counterpart found at low concentrations in complex matrices, in particular in biological samples.

Due to the complexity of the samples (e.g., serum, other bodily fluids, cells, tissues) biomarker discovery remains a very challenging task. The number of chemical and biochemical substances found in the human body is not precisely known. It is certainly a large number, not to mention the enormous variety of molecules in terms of type, shape, size and function. Furthermore, the range of concentration of molecules in biological systems spans many orders of magnitude. Therefore, the use of miniaturized instrumentations and devices in the discovery of protein biomarkers has encounter a number of drawbacks. Traditionally, the analytical chemist would increase the concentration of a sample or inject more sample volume onto a column to get a better signal, thereby increasing the signal strength of one or more analytes of interest and/or their respective modified and/or altered corresponding counterpart. For those substances found at low concentrations, many kinds of amplification procedures have been developed for their analysis. Some of these techniques include immunological and/or non-immunological procedures. Many are coupled to fluorescence detectors for further enhancement of detection. Immunological assays, in particular those using fluorophore-labeled antibodies or antigens, are powerful tools used for medical diagnostics and bioanalytical chemistry because of its high detection sensitivity, non-isotopic safety, multiplexing and quantitative capabilities. In the clinic, miniaturized immuno-analytical devices are designed to move diagnostic testing out of central laboratories into sites closer to the patient.

Capillary electrophoresis (CE) technology, in the conventional and microchip format, has become a powerful tool employed in many laboratories in the search for important biomarkers of diseases. In recent years, increased emphasis has been placed on predictive biomarkers to forecast the origins or future course of toxic events or diseases caused by inflammation. Many organ-specific diseases are preceded by a long preclinical phase that is left undetected by the lack of specific and sensitive assays capable of assessing the early and advanced molecular changes that may cause dysfunction of one or more organs. Detecting a panel of "inflammatory" biomarkers in biological fluids, tissues and cells can have important predictive and confirmatory value depending on the disease and test method under consideration. Furthermore, when referred to pharmaceutical safety and efficacy, the incorporation of biomarkers into the drug development process is becoming a useful tool in the understanding of how new therapies work and allow for more accurate identification of patients who will benefit most from innovative treatments.

The major deficiency of the CE technology for the isolation and quantification of biomarkers of interest is the limits of detection (LOD), which are constrained by the small dimension of the capillary and its reduced pathlength that hinders conventional optical detection methods such as ultraviolet detection. The steps of sample purification and concentration for constituents present primarily in complex samples still remains a bottleneck in the process of sample preparation.

Analyte concentrator-microreactor (ACM) devices have been developed for selective and non-selective molecular consolidations. These analyte concentrator-microreactor (ACM) devices, which are used on-line with a capillary tube or capillary channel, have been described in U.S. Pat. Nos. 5,202,010; 6,406,604; 7,329,388; 7,736,480; 7,811,436; 8,007,724; 8,007,725; and 8,030,092 which are incorporated by references in this disclosure. U.S. Pat. No. 5,741,639 discloses the use of molecular recognition elements. U.S. Pat. No. 5,800,692 discloses the use of a pre-separation membrane for concentrating a sample. U.S. Pat. No. 7,407,568 discloses the use of sol-gel coatings for on-line preconcentration in capillary electrophoresis. U.S. Pat. No. 7,828,948 discloses the use of preconcentration and separation of analytes in microchannels. U.S. Pat. No. 7,959,861 discloses the use of integrated affinity microcolumns and affinity capillary electrophoresis.

While these devices and/or methods fulfill their respective, particular objectives and requirements, it is desirable to provide a new modular and multi-task analyte concentrator-microreactor (ACM) device secured to a portable and interchangeable box that can be mounted peripherally to a capillary electrophoresis instrument for performing on-line affinity capture, purification, preconcentration, microreactions, separation, detection, quantification, identification and characterization of analytes of interest and/or their respective modified and/or altered corresponding counterpart.

Based on these deficiencies, there exists a need for a modular and multi-task device, secured to a portable and interchangeable box, coupled to capillary electrophoresis instrument for affinity purification and having increase sensitivity for polymeric macromolecules and their smaller constituents, in particular proteins and peptides present in complex biological samples.

In these respects, the Modular and Multi-Task analyte concentrator-microreactor (ACM) Device according to the present invention substantially departs from the conventional concepts and designs of the prior art, and in so doing provides a device that when secured to a box body can become portable and interchangeable and capable of being mounted peripherally to capillary electrophoresis or to another instrument used in separation sciences.

OBJECTS OF THE INVENTION

Accordingly, it is a general object of the present invention to provide an improved electrophoresis apparatus having at least a modular analyte concentrator-microreactor (ACM) device to perform on-line preconcentration of an analyte of interest.

It is another object of the present invention that the analyte concentrator-microreactor (ACM) device is connected to one transport capillary or passage with one inlet end and one outlet end to introduce samples and buffers, and one separation capillary with one inlet and outlet ends to separate analytes of interest and/or their respective modified and/or altered corresponding counterpart.

It is a further object of the present invention to secure the modular analyte concentrator-microreactor (ACM) device with the corresponding transport and separation capillaries to a portable and interchangeable box.

An additional object of the present invention is to provide a user-friendly on-line sample preparation system contained in a portable box that can be easily interchangeable when connected and positioned peripherally to a capillary electrophoresis apparatus or another type of instrument capable of performing separation of analytes.

It is yet another object of the present invention to connect the portable and interchangeable box, having an analyte concentrator-microreactor (ACM) device, directly to a detector, such as a mass spectrometer, without the need for a connection to a capillary electrophoresis apparatus or another analytical separation instrument.

It is another object of the present invention that the inlet and outlet ends of the separation passage connected to the analyte concentrator-microreactor (ACM) device can be connected through a coupler or connector to the corresponding inlet and outlet ends of the separation capillary mounted to a cartridge-cassette or support system of the capillaries forming part of a capillary electrophoresis apparatus or another type of commercial or laboratory-made analytical instrument capable of performing separation of analytes to form an integrated system of preconcentration, separation, identification and characterization of analytes of interest and/or their respective modified and/or altered corresponding counterpart.

It is yet another object of the present invention to have an additional modular analyte concentrator-microreactor (ACM) device to perform microreactions where larger polymeric macromolecules are converted into smaller constituents, e.g., cleavage of a protein by an immobilized proteolytic enzyme to generate peptides, or cleavage of a larger polymeric nucleic acid by an immobilized nuclease to generate smaller nucleic acid units.

It is another object of the present invention to have at least a modular analyte concentrator-microreactor (ACM) device to encapsulate cells and/or subcellular components to perform metabolism studies and/or cellular receptors to perform bioactivity studies.

It is a further object of the present invention to couple two or more analyte concentrator-microreactor (ACM) devices, secured to a peripheral box, in-tandem to each other to perform separate and sequentially an on-line microreaction step in the first analyte concentrator-microreactor (ACM) device, and an on-line affinity-capture and preconcentration step of one or more products of the microreaction in the second analyte concentrator-microreactor (ACM) device.

An additional object of the present invention is to separate the released analytes of interest and/or their respective modified and/or altered corresponding counterpart from the preconcentration step in the separation capillary when integrated to a capillary electrophoresis apparatus or another type of instrument capable of performing separation of analytes for further identification and characterization of the analytes of interest and/or their respective modified and/or altered corresponding counterpart.

It is another object of the present invention that one or two analyte concentrator-microreactor (ACM) devices are surrounded by micro-valves to create a controlled microenvironment to perform on-line optimal microreactions or to carry out on-line optimal preconcentrations.

It is yet another object of this invention to provide an integrated system between the peripheral box containing the analyte concentrator-microreactor (ACM) device(s) and the capillary electrophoresis apparatus to provide an electrophoresis apparatus having greater operating efficiency and detectability of the analytes of interest and/or their respective modified and/or altered corresponding counterpart connecting the separation capillary to one or more detectors.

It is a further object of the present invention to provide a color coded box body that is portable and easily interchangeable with another interchangeable box body each containing separate and specific application oriented analyte concentrator-microreactor (ACM) devices. Each device having different affinity ligands to capture and determine different analytes of interest and/or their respective modified and/or altered corresponding counterpart.

It is another object of the present invention to have an analyte concentrator-microreactor (ACM) device connected to an acoustic micromixing system, a microwave pulse system, or a temperature control device to provide optimal mixing and interactions of the immobilized affinity ligands with the analytes of interest and/or their respective modified and/or altered corresponding counterpart and reagents.

It is a further object of the present invention to have an additional, separate and independent, electrical high-voltage power supply and one or two mechanical pumps connected to an auxiliary separation capillary or passage connected through a T-connector to the main separation capillary or passage and positioned downstream of the analyte concentrator-microreactor (ACM) device, to facilitate the separation of the one or more analytes of interest and/or their respective modified and/or altered corresponding counterpart released from the analyte concentrator-microreactor (ACM) device. Introduction of buffers through auxiliary separation capillary or passage connected through a T-connector to the main separation capillary or passage, can enhance the selectivity of analytes of interest and/or their respective modified and/or altered corresponding counterpart and protect the integrity of the affinity ligands immobilized to the beads or microstructures localized within an internal area or channel of the analyte concentrator-microreactor (ACM) device, or immobilized and localized directly to the walls of the internal area of channel of the analyte concentrator-microreactor (ACM) device.

An additional object of the present invention is to have an auxiliary detection system connected to the main separation capillary or passage and positioned downstream of the analyte concentrator-microreactor (ACM) device and upstream of the auxiliary separation capillary or passage.

It is yet another object of the present invention to have a separate and independent port on the analyte concentrator-microreactor (ACM) device and connected through an auxiliary connector to an auxiliary capillary or passage with the purpose of replacing free-standing or free-floating beads or microstructures that are loosely positioned within the internal area or channel of the analyte concentrator-microreactor (ACM) device, to which one or more affinity ligands are immobilized. The replacement of beads or microstructures through this additional separate and independent port connected to the internal area or channel of the analyte concentrator-microreactor (ACM) device and to the auxiliary capillary or passage is crucial to obtain reproducible data, due to multiple times use of the immobilized ligands, damage of the beads or microstructures, or the need for changing different immobilized affinity ligands to capture different peptides of interest. The separate and independent port connected to the auxiliary capillary or passage may serve also as provider of feeding media for maintaining alive cells, subcellular structures and cellular receptors for metabolism and bioassay studies. A further function of the separate and independent port connected to the auxiliary capillary or passage is to serve as an alternative inlet-outlet port for sample and buffer introduction.

It is another object of the present invention to provide a new portable and interchangeable box containing a modular analyte concentrator-microreactor (ACM) device which may be easily and efficiently manufactured and marketed.

SUMMARY OF THE INVENTION

The present invention provides a modular and integrated system in which analyte concentration and/or microreactions are carried out followed by the separation of the analytes of interest and/or their respective modified and/or altered corresponding counterpart. In one aspect of the invention, a sample containing one or more analytes of interest and/or their respective modified and/or altered corresponding counterpart is passed through an analyte concentrator-microreactor (ACM) device localized at an intersection point and connected to a transport capillary and to a separation capillary or channel. The analyte concentrator-microreactor (ACM) device is secured to a peripheral box that is modular and can be integrated with any separation instrument, in particular capillary electrophoresis in capillary or microchip format.

In general, the multi-task analyte concentrator-microreactor (ACM) device can be used for performing a plurality of affinity capturing and enzymatic methods, including synthesis of small molecules and biomolecules. The affinity capturing methods typically bind and retain a wide range of chemical and biochemical substances, cells, subcellular components, globules and other materials. Affinity ligands and/or enzymes are usually immobilized to the inner wall of the analyte concentrator-microreactor (ACM) device or to particles contained within the inner wall of the analyte concentrator-microreactor (ACM) device.

The invention will be more fully described by reference to the following drawings.

DETAILED DESCRIPTION OF THE INVENTION

Figure 1:
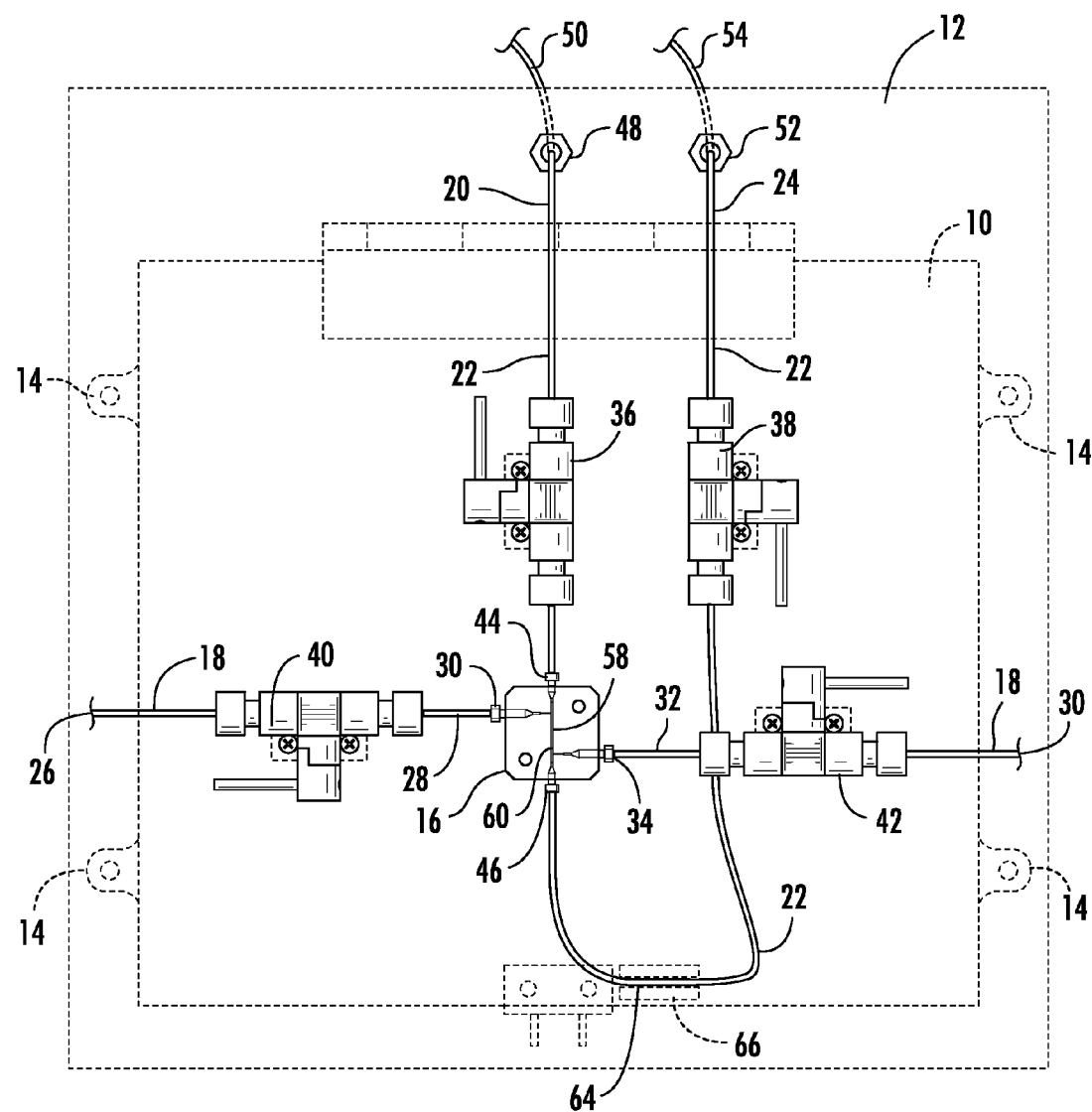
FIG. 1 is an enlarged, elevated front view of a portable an interchangeable box mounted to a support platform having a modular analyte concentrator-microreactor (ACM) device secured to the box body and connected to a transport capillary and a separation capillary, in which the transport capillary and separation capillary are connected to valves. Both the transport capillary and the separation capillary have inlet ends and outlet ends respectively.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 illustrates portable and interchangeable box 10 of the present invention mounted peripherally on side wall or support platform 12 through fastener member 14. Fastener member 14 can be an attachment stud or mechanical fastener. Analyte concentrator-microreactor (ACM) device 16 is secured to portable and interchangeable box 10. Transport capillary or transport passage 18 is connected to analyte concentrator-microreactor (ACM) device 16. Analyte concentrator-microreactor (ACM) device 16 is also connected to inlet area 20 of separation capillary 22 and to outlet area 24 of separation capillary 22. Inlet end 26 of transport capillary 18 serves as a port to introduce a chemical or biological sample, which contains constituents or analytes of interest and/or their respective modified and/or altered corresponding counterpart. Inlet end 26 of transport capillary 18 is also utilized to introduce various buffers to clean and condition the system. Inlet area 28 of transport capillary 18 is connected to analyte concentrator-microreactor (ACM) device 16 through inlet connector 30 of analyte concentrator-microreactor (ACM) device 16, and outlet area 32 of transport capillary 18 is connected to analyte concentrator-microreactor (ACM) device 16 through outlet connector 34. Outlet end 30 of transport capillary 18 is connected to a waste system to collect excess amount of sample and buffers. Analyte concentrator-microreactor (ACM) device 16 is surrounded by four micro-valves 36, 38, 40 and 42 secured to portable and interchangeable box 10 to control the flow of fluids and to create a controlled microenvironment where optimal binding conditions can be obtained. Micro-valves can be operated manually or by an electronically controlled circuitry.

Analyte concentrator-microreactor (ACM) device 16 is connected to inlet area 20 of separation capillary 22, through inlet connector 44. Analyte concentrator-microreactor (ACM) device 16 is connected to outlet area 24 of separation capillary 22, through outlet connector 46, where the actual separation of the released analytes of interest and/or their respective modified and/or altered corresponding counterpart occurs.

Figure 2:
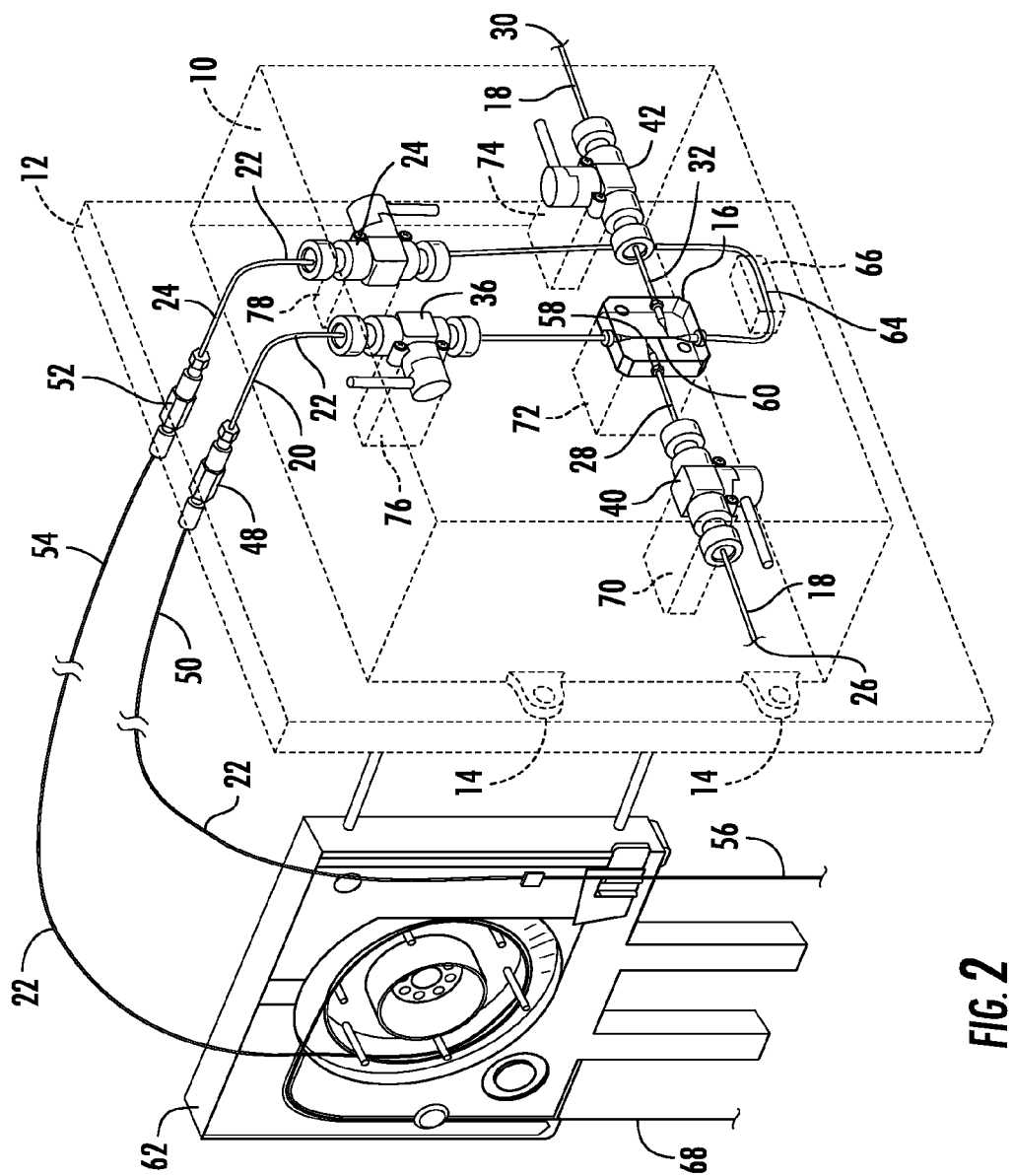
FIG. 2 is a perspective view of a portable an interchangeable box mounted to a support platform having a modular analyte concentrator-microreactor (ACM) device secured to the box body and connected to a transport capillary and a separation capillary, in which the transport capillary and separation capillary are connected to valves, and the inlet and outlet ends of the separation capillary are further connected through couplers to the corresponding inlet and outlet ends of the separation capillary mounted to a cartridge-cassette device of a capillary electrophoresis apparatus or another analytical apparatus used in separation of simple and complex molecules.

Coupler 48 connects inlet area 20 of separation capillary 22 with the corresponding inlet area 50 of separation capillary 22 of cartridge-cassette device 62 of a capillary electrophoresis apparatus, as shown in FIG. 2. The cartridge-cassette device or the capillary electrophoresis apparatus can be a commercial or laboratory-made capillary electrophoresis apparatus. Coupler 52 connects outlet area 24 of separation capillary 22 with corresponding outlet area 54 of separation capillary 22 of cartridge-cassette device 62 of a capillary electrophoresis apparatus. Separation buffer and a plug of an elution buffer or solution are introduced through area 56 of separation capillary 22 of cartridge-cassette device 62, as shown in FIG. 2. If separation of analytes occurs by capillary electrophoresis, the separation can be carried out by one or more of any of the modes of capillary electrophoresis.

Analyte concentrator-microreactor (ACM) device 16 has a cavity or channel forming internal area or channel 58 containing microstructures to which affinity ligands are immobilized. Affinity ligands can also be immobilized directly onto walls 60 of the internal area or channel 58. Affinity ligands can be immobilized to a wide range of material surfaces by modification techniques including covalent and non-covalent methods, including self-assembled monolayer that produce surfaces with well-defined compositions on substrates. Analyte concentrator-microreactor (ACM) device 16 may be configured with a cruciform design containing a short internal channel, or with a staggered design containing a longer channel, as depicted here as internal area or channel 58 of analyte concentrator-microreactor (ACM) device 16 and described in U.S. Pat. Nos. 7,329,388, 8,007,724, 8,007,725, and 8,030, 092. The affinity ligands interacting with analytes of interest and/or their respective modified and/or altered corresponding counterpart can be immobilized directly onto walls 60 of internal area or channel 58 of analyte concentrator-microreactor (ACM) device 16, as described in U.S. Pat. Nos. 7,329, 388, 8,007,724, 8,007,725, and 8,030,092 hereby incorporated by reference in their entireties into this application, or to a matrix-like assembly held within internal area or channel 58 of the type described in U.S. Pat. No. 5,202,010, hereby incorporated by reference in its entirety into this application. The collective mass of the matrix may be provided in many forms by large quantities of microstructures such as beads, platelets, chips, fibers, filaments, monolithic polymers, solgel or the like. Individual substrates can be made from glass, plastic, or other polymeric materials, ceramic, or metallic compositions, and mixtures thereof. Interconnected beaded or polymerized microstructures can form a net or scaffold that can be sustained by itself without the need of a frit structure. All other free-floating microstructures may need a frit structure to be retained within internal area or channel 58 of analyte concentrator-microreactor (ACM) device 16. Covalently or non-covalently affinity ligands coated or immobilized onto the surface of the beaded microstructures, monolithic polymers or sol-gel, or directly onto walls 60 of the inner surface of internal area or channel 58 of analyte concentrator-microreactor (ACM) device 16, are analyte specific antibodies or other type of affinity ligands which are suitable to capture selectively one or more analytes of interest and/or their respective modified and/or altered corresponding counterpart. Non-selective affinity ligands can also be immobilized to the microstructures or directly onto walls 60 of internal area or channel 58 of analyte concentrator-microreactor (ACM) device 16, to capture usually a group of substances with certain physico-chemical properties. Curving section 64 of outlet area 24 of separation capillary 22 is secured to support member 66.

For the experimental conditions to be carried out, it is necessary that micro-valves 36 and 38 are closed and micro-valves 40 and 42 are opened. A simple or complex sample containing analytes of interest and/or their respective modified and/or altered corresponding counterpart can be introduced through transport capillary 18, passing through analyte concentrator-microreactor (ACM) device 16 containing immobilized antibodies in internal area or channel 58 of analyte concentrator-microreactor (ACM) device 16. One or more analytes of interest and/or their respective modified and/or altered corresponding counterpart are retained by the one or more immobilized antibodies. Excess amount of unbound material is washed away by a washing buffer introduced through inlet end 26 of transport capillary 18. At this stage, micro-valves 40 and 42 are closed and micro-valves 36 and 38 are opened. A separation buffer that does not alter the integrity and binding function of the antibodies is passed through the entire separation capillary 22. A plug of an elution buffer or solution is applied in inlet area 56 of separation capillary 22 of cartridge-cassette device 62, as shown in FIG. 2. If separation of analytes occurs by capillary electrophoresis, the separation can be carried out by one or more of any of the modes of capillary electrophoresis. When the plug of an elution buffer is passed through internal area or channel 58 of analyte concentrator-microreactor (ACM) device 16, the bound analytes of interest and/or their respective modified and/or altered corresponding counterpart are released from the antibodies into outlet area 24 of separation capillary 22. The process of separation of the released analytes of interest and/or their respective modified and/or altered corresponding counterpart is performed by electrical principles such as, electro-osmotic flow, mechanical pressure, or a combination of electro-osmotic flow and mechanical pressure. The one or more analytes of interest and/or their respective modified and/or altered corresponding counterpart released by action of the elution buffer from internal area or channel 58 of analyte concentrator-microreactor (ACM) device 16 are then separated, detected, quantified, and characterized, using one or more detectors positioned at outlet end 68 of separation capillary 22 of cartridge-cassette device 62, as shown in FIG. 2.

A similar design depicting analyte concentrator-microreactor (ACM) device 16 with corresponding transport capillary 18, inlet area 20 and outlet area 24 of separation capillary 22, supported to portable and interchangeable box 10 to work with conventional capillary electrophoresis or another analytical separation instrument such as high-performance liquid chromatography (HPLC), gas chromatography or the like, can be adapted with coupler 48 and coupler 52 to work with a microfluidic device such as microchip capillary electrophoresis (Figure not shown).

FIG. 2 illustrates portable and interchangeable box 10 of the present invention mounted peripherally on side wall or support platform 12 through fastener member 14. Inlet area 20 of separation capillary 22 is connected through coupler 48 to inlet area 50 of separation capillary 22 of cartridge-cassette device 62. Separation capillary 22 of cartridge-cassette device 62 is a component of a commercial or laboratory-made capillary electrophoresis apparatus. Outlet area 24 of separation capillary 22 is connected through coupler 52 to outlet area 54 of separation capillary 22 of cartridge-cassette device 62, which is a component of a commercial or laboratory-made capillary electrophoresis apparatus, high-performance liquid chromatography, gas chromatography, microfluidic device, or another analytical separation apparatus, containing one or more detectors of the on-line or off-line type such as ultraviolet, fluorescence, laser-induced fluorescence, mass spectrometer, nuclear magnetic resonance, circular dichroism, electrochemical, conductivity, radioactive or the like. Couplers 48 and 52 and fastener member 14 support and connect portable and interchangeable box 10 peripherally to side wall or support platform 12 and to cartridge-cassette device 62 of a capillary electrophoresis apparatus. When placed together in abutting relation, portable and interchangeable box 10 and cartridge-cassette device 62 define an integral capillary electrophoresis apparatus capable of performing multi-task operations for a wide range of analytes, including capture, purification, concentration, generation of analyte components, derivatization, separation, identification and characterization of analytes of interest and/or their respective modified and/or altered corresponding counterpart having appropriate detectors for enhancing sensitivity and providing structural information. However, all connecting parts of the components of portable and interchangeable box 10 must be tightly connected, avoiding any possibilities of leakages of fluid exit and of air penetration to the capillary passage systems. Support components 66, 70, 72, 74, 76 and 78 facilitate the coordinated assembly of transport capillary 18, inlet area 20 and outlet area 24 of separation capillary 22 to analyte concentrator-microreactor (ACM) device 16 within portable and interchangeable box 10, and to micro-valves 36, 38, 40 and 42. Couplers 48 and 52 provide assembly and connection to cartridge-cassette device 62. Portable and interchangeable box 10, containing analyte concentrator-microreactor (ACM) device 16, micro-valves 36, 38, 40 and 42, transport capillary 18, inlet area 20 and outlet area 24 of separation capillary 22, provides a portable and easy interchangeable casing protective system that can be color coded to indicate that each box contains one exclusive analyte concentrator-microreactor (ACM) device 16 allocated to perform one or more particular applications. The analyte concentrator-microreactor (ACM) device can be color coded as well, or the color coded identification or classification can be carried out for both the portable and interchangeable box and the analyte concentrator-microreactor (ACM) device to indicate a certain operation, use and/or application. The use of analyte concentrator-microreactor (ACM) device 16 in FIGS. 1 and 2 is primarily configured to function as a concentrator device, but it can also be used as a microreactor where, for example, proteolytic enzymes can be immobilized to microstructures or wall contained within the cavity of analyte concentrator-microreactor (ACM) device 16 to cleave proteins to generate peptides. Furthermore, the analyte concentrator-microreactor (ACM) device can provide a microenvironment to encapsulate cells and cellular structures to perform metabolism studies, and to encapsulate cellular receptors to perform bioassay studies.

The analytes of interest and/or their respective modified and/or altered corresponding counterpart can include biological and non-biological affinity ligands, such as intact antibodies, single-chain antibodies, antibody fragments, antigens, protein A, protein G, lectins, glycoproteins, glycolipids, enzymes, substrates, cofactors, coenzymes, drugs, vitamins, hormones, proteins, viruses, cells, subcellular structures, cell components, prions, receptors, membranes, dyes, metal-containing moieties, organometallic moieties, synthetic ligands or the like. The analytes of interest and/or their respective modified and/or altered corresponding counterpart can include biological and non-biological analytes present in simple and complex matrices, such as intact antibodies, antibody fragments, antigens, protein A, protein G, lectins, glycoproteins, glyco lipids, enzymes, substrates, cofactors, coenzymes, drugs, vitamins, hormones, proteins, viruses, cells, subcellular structures, cell components, prions, receptors, membranes, dyes, metal-containing moieties, organometallic moieties, synthetic ligands or the like.

In order to provide a microenvironment with optimal conditions for the interaction between the immobilized affinity ligands, the analytes of interest and/or their respective modified and/or altered corresponding counterpart and other reagents it is used a micromixing system, a microwave pulsing system, and/or a temperature controlled system. The accessories can be annexed to the analyte concentrator-microreactor (ACM) device (FIG. not shown).

Another alternative use for the portable and interchangeable box, having a modular analyte concentrator-microreactor (ACM) device, is to attach the unit directly to a detector such as a mass spectrometer, without the need for connecting the unit to a capillary electrophoresis apparatus or another analytical separation instrument.

A safety cover or enclosure is provided to the portable and interchangeable box (FIG. not shown) to protect against specified external conditions such as fluid spill and to prevent electric shock. The addition of safety sensor will make the integrated capillary electrophoresis apparatus or another analytical separation instrument inoperable during sample and buffers introduction.

The portable and interchangeable box and/or the analyte concentrator-microreactor (ACM) device can be color-coded to represent the presence of specific affinity ligands and/or a particular functionality. For example, it can used for the determination of a certain number of analyte biomarkers associated to the diagnosis and/or prognosis of a particular disease or toxic state, and/or to identify the normality-abnormality of a certain organ, tissue, cluster cells, or circulating cell.

Figure 3:
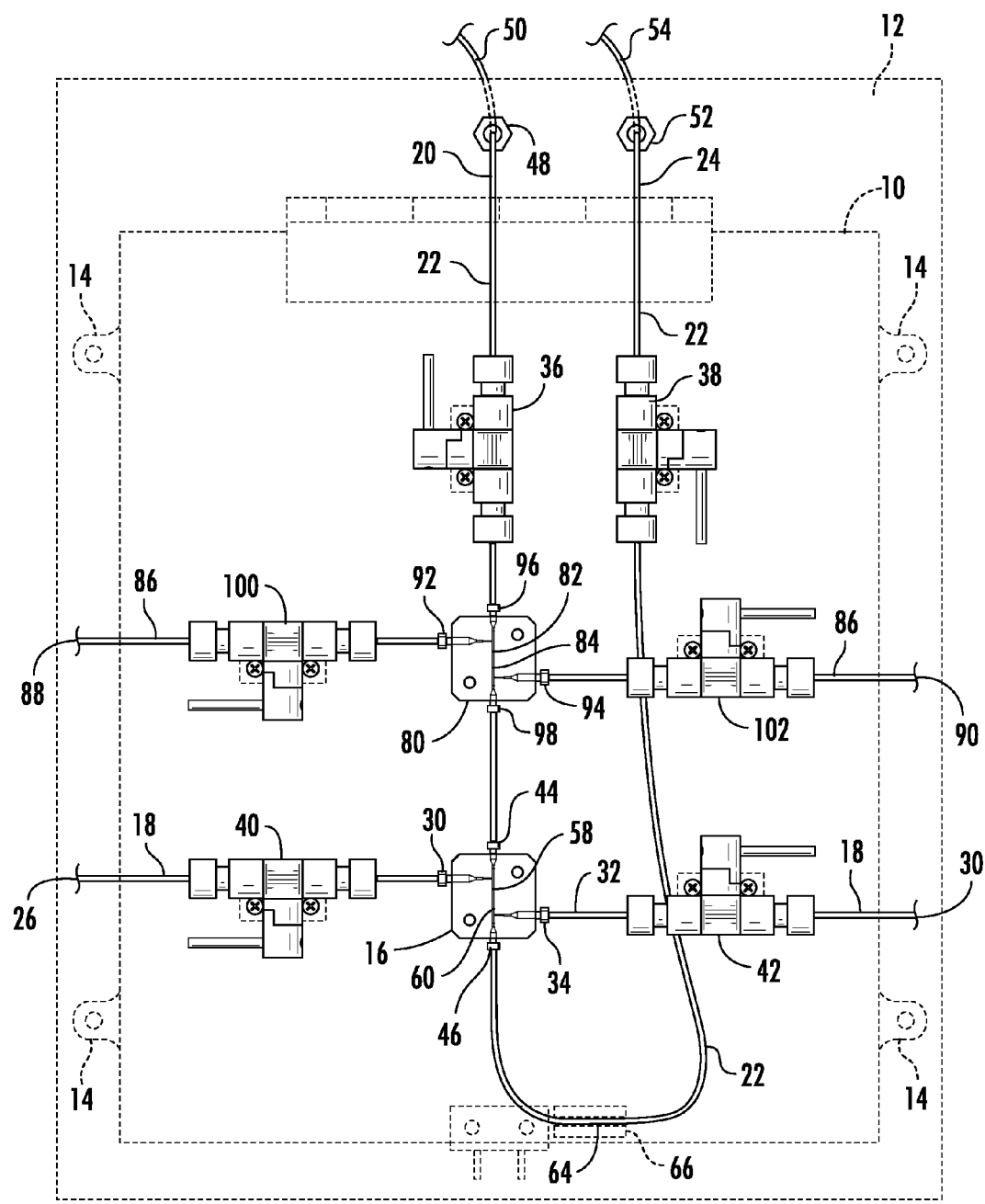
FIG. 3 is an enlarged, elevated front view of a portable an interchangeable box mounted to a support platform having two modular analyte concentrator-microreactor (ACM) devices secured to the box body and each analyte concentrator-microreactor (ACM) device is connected separately and independently to a corresponding transport capillary having inlet and outlet ends. There is also a single separation capillary with an inlet end and an outlet end connected to the two analyte concentrator-microreactor (ACM) devices. Furthermore, both transport capillaries and the separation capillary are connected to corresponding valves.

FIG. 3 illustrates portable and interchangeable box 10 of the present invention mounted peripherally on side wall or support platform 12 through fastener member 14. Portable and interchangeable box 10 in this design has two analyte concentrator-microreactor (ACM) devices. Analyte concentrator-microreactor (ACM) device 80 that is used to function as a microreactor, and another analyte concentrator-microreactor (ACM) device 16 is used to function as a concentrator. In internal area or channel 82 of analyte concentrator-microreactor (ACM) device 80, microstructures can be positioned to which a proteolytic enzyme can be immobilized, or the proteolytic enzyme can be immobilized directly onto walls 84 of internal area or channel 82 of analyte concentrator-microreactor (ACM) device 80. A simple or complex sample containing proteins (e.g., serum) can be introduced through transport capillary 86 from inlet end 88 to outlet end 90 of transport capillary 86 passing through analyte concentrator-microreactor (ACM) device 80. Transport capillary 86 is connected to analyte concentrator-microreactor (ACM) device 80 through inlet connector 92 and outlet connector 94. Analyte concentrator-microreactor (ACM) device 80 is also connected to inlet area 20 of separation capillary 22 through inlet connector 96 and outlet connector 98. Once the sample containing proteins (e.g., serum) is parked within internal area or channel 82 for a certain period of time and at certain optimization conditions of temperature and mixing of reagents, cleavage of the proteins occur within internal area or channel 82 of analyte concentrator-microreactor (ACM) device 80.

A microenvironment is created by opening and closing the respective micro-valves 36, 38, 40, 42, 100 and 102 surrounding analyte concentrator-microreactor (ACM) devices 80 and 16. In this particular configuration, in order for the sample to be introduced through transport capillary 86, micro-valves 40 and 42 connecting analyte concentrator-microreactor (ACM) device 16 to transport capillary 18 must be closed, and micro-valves 36 and 38 connecting inlet area 20 and outlet area 24 of separation capillary 22 must be closed as well. Micro-valves 100 and 102 are the only ones opened for sample introduction. The sample, containing the one or more analytes of interest and/or their respective modified and/or altered corresponding counterpart, is transported from inlet end 88 of transport capillary 86 to outlet end 90 passing through internal area or channel 82 of analyte concentrator-microreactor (ACM) device 80. Once the sample has been passed through the entire transport capillary 86, micro-valves 100 and 102 surrounding analyte concentrator-microreactor (ACM) device 80 are closed as well to create a microenvironment in internal area or channel 82 of analyte concentrator-microreactor (ACM) device 80 where the proteins of the sample will be cleaved to generate peptides.

Under normal experimental operation, inlet area 20 and outlet area 24 of separation capillary 22 are filled with separation buffer. All four micro-valves 40, 42, 100 and 102 surrounding analyte concentrator-microreactor (ACM) devices 80 and 16 are maintained closed and micro-valves 36 and 38 connected to inlet area 20 and outlet area 24 of separation capillary 22 are opened. The electrophoresis separation process can start where all peptides generated in analyte concentrator-microreactor (ACM) device 80 will pass through analyte concentrator-microreactor (ACM) device 16 containing an antibody immobilized to microstructures positioned within internal area or channel 58 of analyte concentrator-microreactor (ACM) device 16. The antibody can also be immobilized directly to walls 60 of internal area or channel 58 of analyte concentrator-microreactor (ACM) device 16. The antibody can be directed against one particular analyte of interest (e.g., one of the peptides generated in the cleavages of all proteins present in the serum), or it can be directed to a family of related peptides, or it can be directed to a certain group of peptides having one or more post-translational modifications of proteins (e.g., methylation, acetylation, phosphorylation, and the like.). Alternatively, two or more antibodies can be immobilized in the same internal area or channel 58 of analyte concentrator-microreactor (ACM) device 16, as described in U.S. Pat. Nos. 7,329,388, 8,007,724, 8,007,725, and 8,030,092.

The separation of the peptides can be carried out by electrical principles, electro-osmotic flow, mechanical pressure, or a combination of electro-osmotic flow and mechanical pressure. Under these experimental conditions, the separation buffer is mild and does not alter the integrity of the immobilized one or more antibodies. Therefore, one or more analytes of interest and/or their respective modified and/or altered corresponding counterpart are retained by the one or more antibodies immobilized within internal area or channel 58 of analyte concentrator-microreactor (ACM) device 16. Once all peptides non-retained by the antibodies within internal area or channel 58 of analyte concentrator-microreactor (ACM) device 16 are separated in the actual separation portion of separation capillary 22, starting after analyte concentrator-microreactor (ACM) device 16 all the way to outlet area 68 of cartridge-cassette device 62 and the separated peptides are detected by one or more detectors positioned at cartridge-cassette device 62, a plug of an elution buffer or solution is applied in inlet area 56 of separation capillary 22. The process of separation of the peptides continue to be performed by the same separation buffer conditions and using electrical principles, electro-osmotic flow, mechanical pressure, or a combination of electro-osmotic flow and mechanical pressure. The one or more analytes of interest and/or their respective modified and/or altered corresponding counterpart released by action of the elution buffer from internal area or channel 58 of analyte concentrator-microreactor (ACM) device 16 are then separated, detected, quantified, identified, and characterized. The elution buffer or solution can also contain a tagging reagent or dye that when in contact with the antibody-analyte of interest complex can release and derivatize the peptide or analyte of interest simultaneously. The resulting derivatized peptide can have improved selectivity and detectability.

Transport capillaries 86 and 18 and inlet area 20 and outlet area 24 of separation capillary 22 can be regenerated and conditioned for a new cycle of operation.

Figure 4:
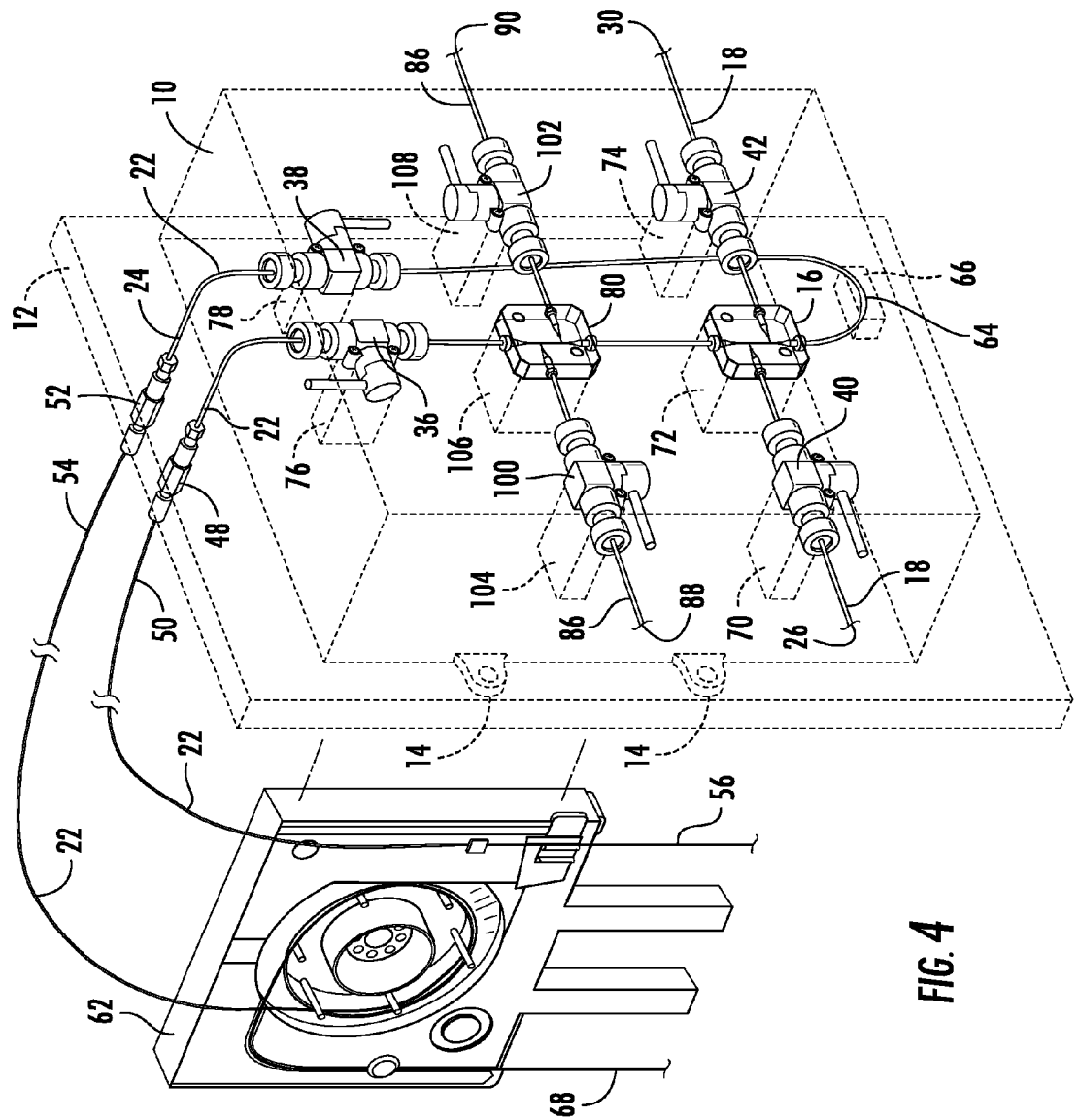
FIG. 4 is a perspective view of a portable an interchangeable box mounted to a support platform having two modular analyte concentrator-microreactor (ACM) devices secured to the box body and each analyte concentrator-microreactor (ACM) device is connected separately and independently to a corresponding transport capillary having inlet and outlet ends. There is also a single separation capillary with an inlet end and an outlet end connected to the two analyte concentrator-microreactor (ACM) devices. Furthermore, both transport capillaries and the separation capillary are connected to corresponding valves. In addition, the inlet and outlet ends of the separation capillary are further connected through couplers to the corresponding inlet and outlet ends of the separation capillary of a cartridge-cassette device of a capillary electrophoresis apparatus or another analytical apparatus used in separation of simple and complex molecules.

FIG. 4 illustrates a more comprehensive view of portable and interchangeable box 10 connected to cartridge-cassette device 62. Portable and interchangeable box 10 is mounted peripherally on side wall or support platform 12 through fastener member 14. Portable and interchangeable box 10 in this design has two analyte concentrator-microreactor (ACM) devices, analyte concentrator-microreactor (ACM) device 80 that is used to function as a microreactor, and another analyte concentrator-microreactor (ACM) device 16 that is used to function as a concentrator. Each analyte concentrator-microreactor (ACM) device is connected separately and independently to transport capillaries 86 and 18 and to inlet area 20 and outlet area 24 of separation capillary 22. Furthermore, analyte concentrator-microreactor (ACM) devices 80 and 16 are controlled by micro-valves 36, 100, 102, 40, 42 and 38. Micro-valves 100, analyte concentrator-microreactor (ACM) device 80, and micro-valve 102 are supported to support members 104, 106 and 108 respectively.

Analyte concentrator-microreactor (ACM) device 80 is used to perform microreactions, and analyte concentrator-microreactor (ACM) device 16 is used to perform affinity concentration using selective affinity ligands such as antibodies, lectins, aptamers, or other non-selective affinity ligands such as ionic exchangers, dyes, C18, C8, etc. Other experimental procedures can be carried out as described above with reference to FIG. 3.

The portable and interchangeable box and/or the analyte concentrator-microreactor (ACM) device can be color-coded to represent the presence of specific affinity ligands and/or a particular functionality. For example, it can used for the determination of a certain number of peptide and/or nucleotide biomarkers associated to the diagnosis and/or prognosis of a particular disease or toxic state, and/or to identify the normality-abnormality of a certain organ, tissue, cluster cells, or circulating cell.

Figure 5:
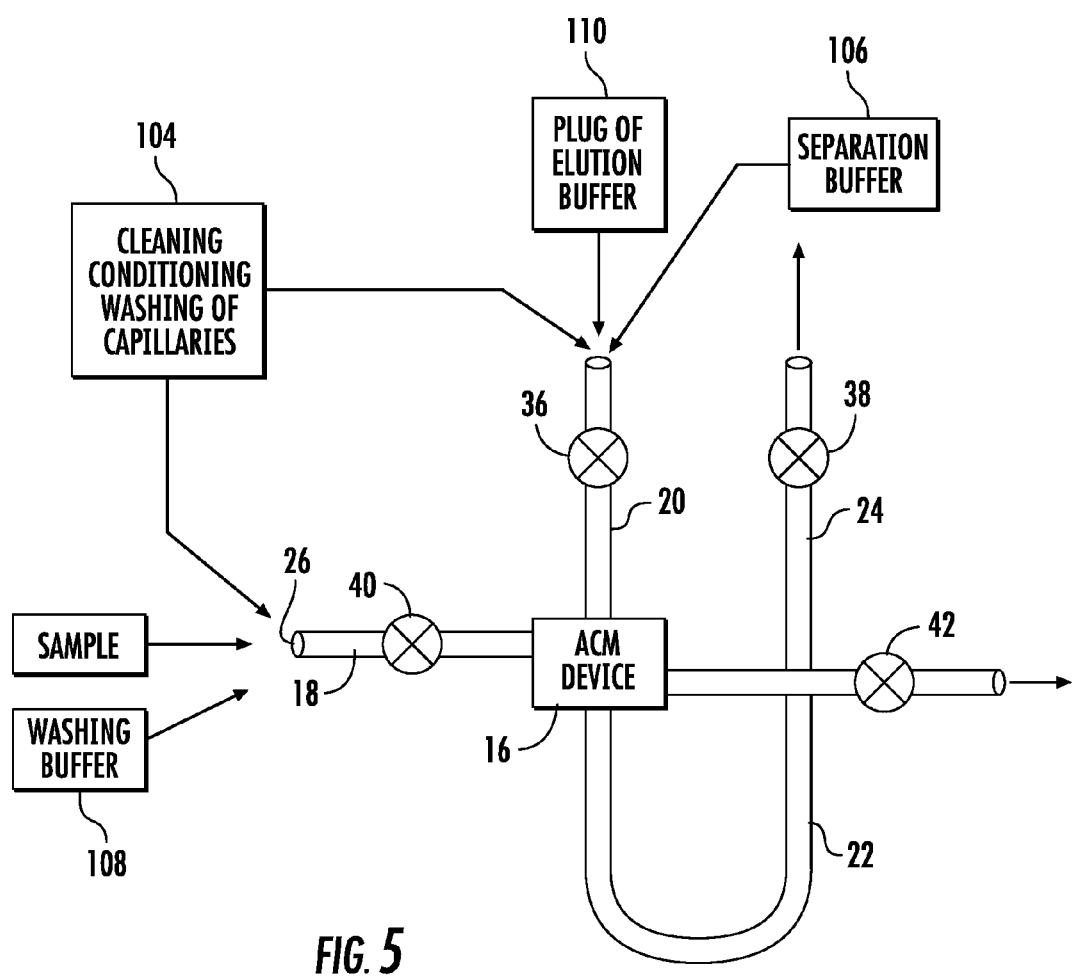
FIG. 5 is a schematic representation of the sequence of events describing the cleaning and conditioning of the transport and separation capillaries, and the inner cavity or channel of the analyte concentrator-microreactor (ACM) device, prior to sample introduction. The washing of the transport and separation capillaries, and the inner cavity or channel of the analyte concentrator-microreactor (ACM) device after sample introduction, and the process of elution or release of the one or more analytes of interest and/or their respective modified and/or altered corresponding counterpart bound to the analyte concentrator-microreactor (ACM) device. The released analytes of interest and/or their respective modified and/or altered corresponding counterpart are then separated in the separation capillary.

FIG. 5 illustrates the sequence of events required to perform solid phase extraction using immunoaffinity capillary electrophoresis for the purification and concentration of a wide range of analytes, including small molecular weight analytes, biomolecules, cells, subcellular components, virus, prions, globular materials and the like. When separation capillary 22 connected to analyte concentrator-microreactor (ACM) device 16, containing immobilized affinity ligands, is coupled to another set of separation capillary, either attached to a support or contained within a cartridge-cassette of a commercial or laboratory-made capillary electrophoresis apparatus or any other analytical separation instrument, such as nano-HPLC, a powerful tool is generated for affinity capture, purification, derivatization, separation, detection, quantification and characterization of a wide range of molecules present in simple and complex mixtures at low, intermediate, or high concentrations.

As described in previous figures, the core of the invention is an analyte concentrator-microreactor (ACM) device 16 capable of performing on-line micro-reactions or micro-concentrations. If analyte concentrator-microreactor (ACM) device 16 is used as a micro-reactor or micro-concentrator, microstructures are positioned within its interior cavity or channel to which affinity ligands are immobilized. The microstructures can be retained by porous plugs or frits, they can be polymerized without the need for frits, or they can be connected to each other and to the walls of the inner cavity or channel without the need for frits. Affinity ligands can be immobilized to the microstructures by non-covalent or covalent attachment. The affinity ligands can be, for example, antibodies to capture selectively one or more analyte of interest, or they can be, for example, proteolytic enzymes to cleave proteins and generate peptides. Affinities can be classified as high affinity ligand binding and low affinity ligand binding. In general, high affinity ligand binding results from greater intermolecular force between the ligand and its receptor while low affinity ligand binding involves less intermolecular force between the ligand and its receptor. Certain ligands can also bind to analytes non-selectively, binding to a set of molecules with certain similar physical-chemical properties.

Analyte concentrator-microreactor (ACM) devices 80 and 16 are dependent of the coordination of operation of all six micro-valves 36, 38, 40, 42, 100, and 102, as shown in FIG. 4, to control the flow of fluids and to create a microenvironment for optimization of experimental conditions. Portable and interchangeable box 10 is assembled and the segmented separation capillary 22 is connected to cartridge-cassette device 62 through couplers 48 and 52 to a commercial or laboratory-made capillary electrophoresis apparatus, or other analytical separation instrumentations, as shown in FIG. 2. Referring to FIG. 5, the first step 104 in the sequence of events is to clean entirely transport capillary 18 and separation capillary 22, from inlet area 56 through outlet area 68 of cartridge-cassette device 62 and portable and interchangeable box 10, when micro-valves 40 and 42 are closed and micro-valves 34 and 36 are open, as shown in FIG. 2. It is important to check for any leakage. The system should operate completely sealed in a closed circuit and avoid any formation of bubbles. All buffers must be degassed before use. Once the cleaning is completed, using an appropriate cleaning buffer or solution, usually a buffer containing high salt concentration and mild detergents, an optimization buffer is followed. The cleaning and optimization buffers are also introduced to transport capillary 18, when micro-valves 36 and 38 are closed and micro-valves 40 and 42 are open. The optimization buffer should be mild to protect the integrity and functionality of the immobilized affinity ligands.

In step 106 referring to FIG. 5 of the experimental procedure, micro-valves 40 and 42 are closed and micro-valves 36 and 38 are opened and separation capillary 22 is entirely filled with a mild separation buffer. For example, the separation buffer can be 50 to 100 millimolar concentration of sodium tetraborate buffer pH 8.3. If analyte concentrator-microreactor (ACM) device 16 is used as a micro-concentrator, the analyte concentrator-microreactor (ACM) device 16 should contain one or more affinity ligands to capture one or more analytes of interest and/or their respective modified and/or altered corresponding counterpart. A simple or complex sample, containing one or more analytes of interest and/or their respective modified and/or altered corresponding counterpart, is introduced from inlet end 26 of transport capillary 18 through outlet end 30 of transport capillary 18 connected to a waste container, and the sample passed by the inner area of analyte concentrator-microreactor (ACM) device 16 containing one or more immobilized antibodies, and/or another affinity ligand. Micro-valves 36, 38, 40, and 42 are closed, to create a closed microenvironment, and a certain time of incubation is allowed to obtain maximum binding between the analyte(s) and the antibody(s) and/or other affinity ligands. A controlled temperature and motion of reactants is allowed for further optimization of the binding. In step 108, micro-valves 40 and 42 are opened and micro-valves 36 and 38 are closed, and a mild washing buffer is introduced through the entire transport capillary 18 with the purpose of eliminating excess amount of sample, and unwanted non-specifically bound substances. Once this step is completed, micro-valves 40 and 42 are closed and micro-valves 36 and 38 are opened in order to start the process of elution and separation.

In step 110, a small plug of an elution or desorption buffer or solution is introduced from a small container or cup localized in inlet area 56 of separation capillary 22 located at the very inlet of separation capillary 22 positioned at cartridge-cassette device 62 of the capillary electrophoresis apparatus, as shown in FIG. 2. The same separation buffer that is in the separation capillary is introduced immediately after the plug of elution buffer. A separation buffer positioned in a separate container or cup, and the introduction of all buffers are carried out in a coordinated fashion. A process of separation is started at a desired voltage and amperage. The process of separation is carried out using electrical migration principles, electro-osmotic flow, mechanical pressure, or a combination of electro-osmotic flow and mechanical pressure. Once the plug of elution buffer passes through the inner area of analyte concentrator-microreactor (ACM) device 16, the one or more analytes of interest and/or their respective modified and/or altered corresponding counterpart bound to the immobilized affinity ligand(s) are released by action of the elution buffer from the internal area of analyte concentrator-microreactor (ACM) device 16 are then separated in separation capillary 22. At outlet area of separation capillary 22, after outlet area 54 and before inlet end 56, usually at a point of the cartridge-cassette, one or more detection systems can be connected to separation capillary 22 by direct contact or through a fiber optic system. The separated analytes of interest and/or their respective modified and/or altered corresponding counterpart are now detected, quantified, identified and characterized. A new cycle of operation can be started by cleaning the system as described above.

In the case that the analyte concentrator-microreactor (ACM) device 16 is used as a micro-reactor system, a proteolytic enzyme can be immobilized to internal area or channel 58 of analyte concentrator-microreactor (ACM) device 16. The procedure is the same, except that each proteolytic enzyme requires different buffer conditions to operate at optical effectiveness. A sample containing proteins is introduced through transport capillary 18, micro-valves 36 and 38 are then opened and micro-valves 40 and 42 are closed, and the proteins in the sample are allowed to park for a certain period of time. All four micro-valves are now closed to create a complete closed micro-environment. Temperature and motion of reactants can also be allowed. Micro-valves 36 and 38 are opened and the process of separation and detection is performed as described above. Instead of proteolytic enzymes, other enzymes can be used to cleave other polymers, such as complex polymeric nucleotides or sugars. Furthermore, peptide synthesis or synthesis of other molecules is permitted to be carried out in these micro-reactors.

In the case that analyte concentrator-microreactor (ACM) device 16 is used as a micro-concentrator, cells can be captured from blood samples or other complex biofluids containing cells or cellular structures for identification and quantification purposes or to perform metabolism studies, or bioassays.

Figure 6:
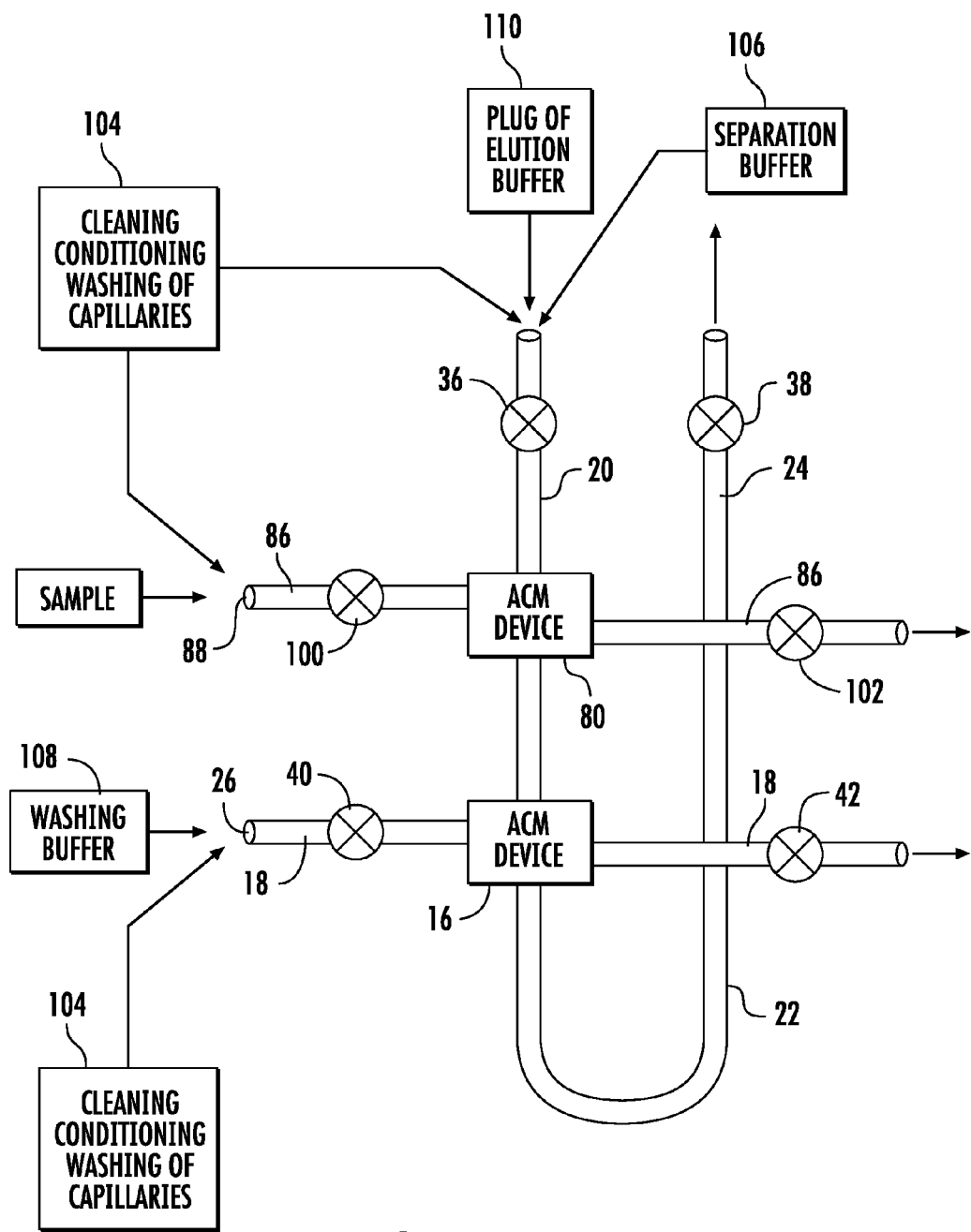
FIG. 6 is a schematic representation of the sequence of events required to perform two biochemical-immunological processes on-line, one of which is enzymatic cleavage of protein constituents present in a simple and complex sample, followed by a second process of affinity capture of one or more peptides of interest generated in the first process. The two processes are carried out using two analyte concentrator-microreactor (ACM) devices. In the first analyte concentrator-microreactor (ACM) device, the enzymatic cleavage of a protein is carried out by a proteolytic enzyme immobilized to microstructures positioned within the inner area or channel, or immobilized directly to the walls of the inner area or channel of the first analyte concentrator-microreactor (ACM) device. Alternatively, a nuclease enzyme can be immobilized in the first analyte concentrator-microreactor device with the purpose of cleaving larger nucleic acid components, such as deoxyribonucleic acid (DNA) or ribonucleic acid (RNA) into smaller nucleic acid units. In the second analyte concentrator-microreactor (ACM) device, the affinity capture is carried out by one or more affinity ligands immobilized to microstructures positioned within the inner area or channel, or immobilized directly to the walls of the inner area or channel of the second analyte concentrator-microreactor (ACM) device. Prior to sample introduction and cleavage of the proteins and affinity-capture of the selected generated peptides, a series of cleaning, conditioning and washing steps are performed. Release of the bound peptides of interest is carried out by a plug of an elution buffer or solution, followed by separation, detection, quantification, identification and characterization of peptides. Alternatively, affinity capture of the generated smaller nucleic acid units can be carried out in the second analyte concentratot-microreactor (ACM) device.

FIG. 6 illustrates the sequence of events required to perform on-line protein digestion in the first of two analyte concentrator-microreactor (ACM) devices 80 utilized in this protocol, followed by capture of two or more peptides by one or more affinity ligands immobilized to the second analyte concentrator-microreactor (ACM) device 16. Prior to perform these two enzymatic-immunological reactions, a similar cleaning and conditioning experimental procedure described for FIG. 5 is carried out for FIG. 6.

In step 104 referring to FIG. 6, a schematic representation of the sequence of events is described for cleaning and conditioning of two transport capillaries and one separation capillary intersecting with the two transport capillaries, as well as the cleaning and conditioning of the walls and/or particles-microstructures positioned within the internal cavity or channels of the two analyte concentrator-microreactor (ACM) devices, prior to sample introduction. In the first step 104, micro-valves 40 and 42 connected to transport capillary 18 are closed and micro-valves 100 and 102 connected to transport capillary 86, and micro-valves 36 and 38 connected to separation capillary 22 are opened. Cleaning buffer or solution is introduced followed by conditioning buffer to transport capillary 86 and separation capillary 22 entirely, including the separation capillary mounted to the cartridge-cassette device forming part of capillary electrophoresis apparatus as shown in FIG. 4, or any other analytical separation instrument. Thereafter, micro-valves 40 and 42 are opened and micro-valves 100, 102, 36, and 38 are closed. Cleaning buffer or solution is introduced followed by conditioning buffer to transport capillary 18. The walls and/or particles-microstructures within the internal cavity or channel of analyte concentrator-microreactor (ACM) devices 80 and 16 are now completely cleaned. If separation of analytes occurs by capillary electrophoresis, the separation can be carried out by one or more of any of the modes of capillary electrophoresis.

In step 106, referring to FIG. 6 of the experimental procedure, separation capillary 22 is filled entirely with a mild separation buffer capable of maintaining the integrity of the enzyme immobilized to analyte concentrator-microreactor (ACM) device 80 and of the affinity ligands immobilized to analyte concentrator-microreactor (ACM) device 16. However, it is expected that the mild separation buffer of separation capillary 22 provides sufficient beneficial properties to separate the released peptides of interest with enhanced selectivity, yet permitting multiple uses of the immobilized enzyme and affinity ligands to their respective analyte concentrator-microreactor (ACM) devices 80 and 16.

Immobilized enzymes to a solid support, called also insolubilized enzymes, show increased thermal and pH stability and can be employed for extended period of time without loss of activity.

A simple or complex sample containing proteins is passed through first transport passage 86 from its inlet end 88 and the first analyte concentrator-microreactor (ACM) device 80, when micro-valves 100 and 102 are opened and micro-valves 36, 38, 40 and 42 are closed. Once the sample has filled transport capillary 86 entirely, micro-valves 40 and 42 are closed generating a micro-environment in internal area or channel 82 of analyte concentrator-microreactor (ACM) device 80. Sample is parked for a certain period of time, usually less than about 5 minutes, and control of temperature and motion of reagents can be carried out as described in U.S. Pat. Nos. 7,329,388; 8,007,724; 8,007,725; and 8,030,092, in order to provide optimal conditions for cleavage of proteins present in the sample. At this stage, micro-valves 36 and 38 are opened and micro-valves 100, 102, 40 and 42 remain closed. A process of separation is started, using electrical principle migration, electro-osmotic flow, mechanical pressure, or a combination of electro-osmotic flow and mechanical pressure. All peptides generated by the proteolytic digestion on analyte concentrator-microreactor (ACM) device 80 will be separated within separation capillary 22 and monitored by the one or more detectors localized at the cartridge-cassette device 62 of the integrated capillary electrophoresis apparatus, or another analytical instrument capable of separating peptides, as shown in FIG. 4, except for those peptides captured by the affinity ligands immobilized on analyte concentrator-microreactor (ACM) device 16.

In step 108, referring to FIG. 6 of the experimental procedure, a mild washing buffer is introduced to remove unwanted materials or substances bound non-specifically to transport capillary 18 and to inner area or channel 58, as shown in FIG. 4. In step 110, referring to FIG. 6 of the experimental procedure, a small volume or plug of an elution buffer or solution is introduced in inlet end 56 of separation capillary 22, as shown in FIG. 4, followed by the same separation buffer used for the separation of the non-captured peptides. The experimental protocol of separation and detection of the affinity-captured peptides by the immobilized affinity ligands within the internal area or channel of the analyte concentrator-microreactor (ACM) device is identical as the protocol described for the non-captured peptides.

Figure 7:
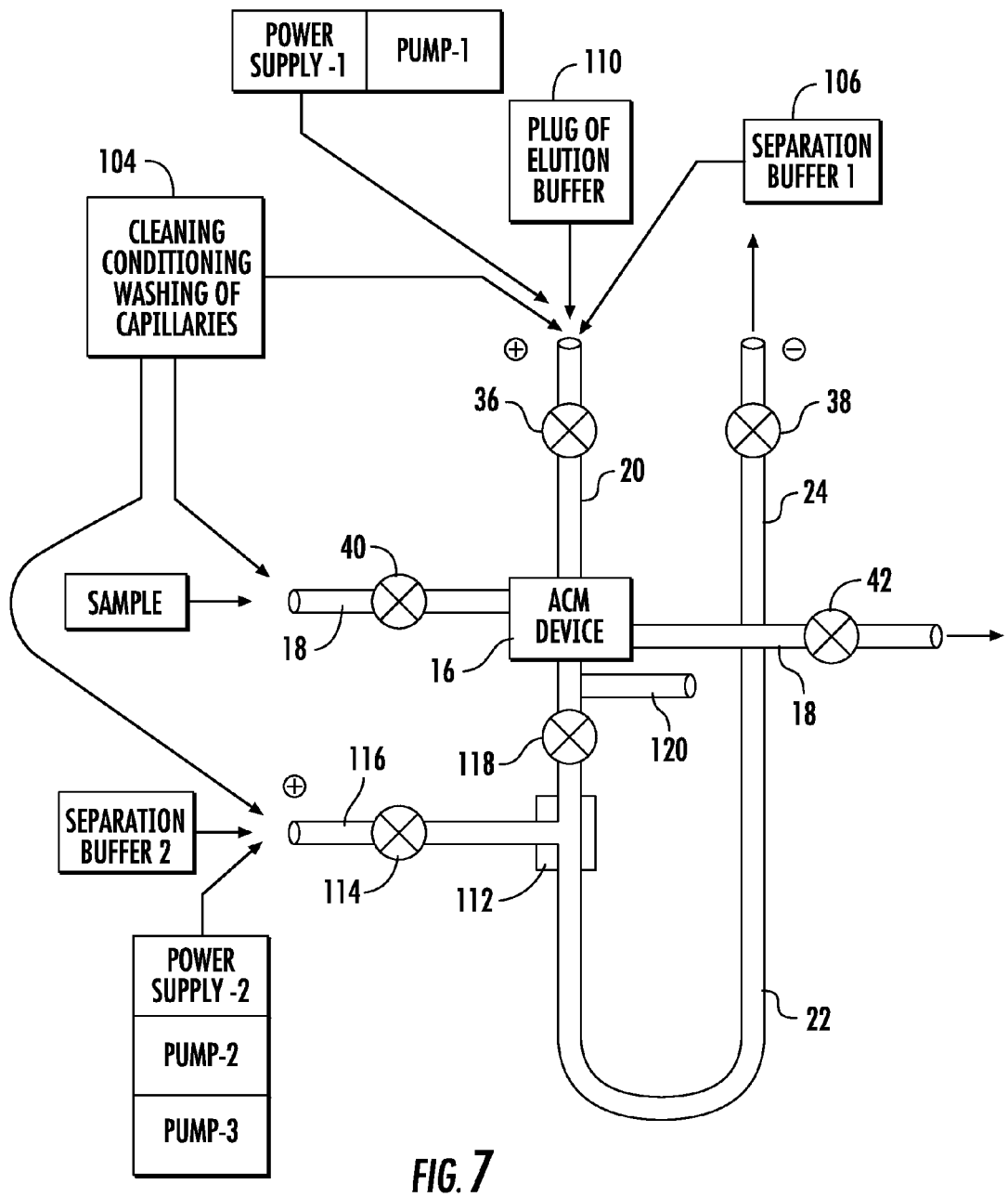
FIG. 7 is a schematic representation of the sequence of events required to perform on-line affinity capture of one or more analytes of interest and/or their respective modified and/or altered corresponding counterpart using an analyte concentrator-microreactor (ACM) device, followed by the release of the reversible bound analytes and the separation, detection, quantification, identification and characterization of analytes of interest and/or their respective modified and/or altered corresponding counterpart. The schematic representation shows also the presence of an auxiliary passage connected to a separation capillary, two high-voltage power supplies, and three mechanical pumps to perform a mild affinity-capture process employing buffers not affecting the integrity of the immobilized affinity ligands. The auxiliary passage depicted in the schematic of FIG. 7, and localized downstream of analyte concentrator-microreactor (ACM) device, provides a separation buffer that enhance the separation of the released affinity capture analytes, but may compromise the integrity of the immobilized affinity ligands. The design of this device or unit allows the protection and re-use of the immobilized affinity ligands multiple times.

FIG. 7 illustrates the sequence of events required to perform under optimal experimental conditions on-line affinity capture of one or more analytes of interest and/or their respective modified and/or altered corresponding counterpart present in a simple or complex sample. Furthermore, FIG. 7 describes the protocol to perform under optimal experimental conditions the separation of the released analytes of interest and/or their respective modified and/or altered corresponding counterpart from analyte concentrator-microreactor (ACM) device 16, without compromising the integrity of the affinity ligands immobilized to analyte concentrator-microreactor (ACM) device 16. The protocol to clean and condition transport capillaries 18, and auxiliary separation capillary or passage 116, main separation capillary 22 and analyte concentrator-microreactor (ACM) device 16 is basically similar or identical to the protocol described in FIG. 5.

Once all passages are cleaned and conditioned, micro-valves 40, 42 and 114 are closed, and microvalves 36, 38 and 118 are opened. In step 106, a mild separation buffer-1 is introduced from inlet end 56 of separation capillary 22 mounted on cartridge-cassette device 62 entirely to outlet end 68, as shown in FIGS. 2 and 4. The mild separation buffer-1 will allow optimal conditions of binding between the immobilized affinity ligands and the one or more analytes of interest and/or their respective modified and/or altered corresponding counterpart. At this stage, micro-valves 36 and 118 are closed; micro-valves 40 and 42 remain closed, micro-valve 38 remains opened, and valve 114 is opened. A strong separation buffer-2 is introduced from inlet end of auxiliary separation capillary 116 through main separation capillary 22 entirely to outlet end 68, as shown in FIGS. 2 and 4. Auxiliary separation capillary or passage 116 is connected to separation capillary 22 using a connecting T-shaped coupler or T-connector 112. The separation buffer-2 can contain additives such as cyclodextrins, organic solvents, detergents, chaotropic agents and/or chelating agents that may provide high shape selectivity for high-efficiency separation of the analytes of interest and/or their respective modified and/or altered corresponding counterpart. Separation buffer-2 is positioned downstream of the analyte concentrator-microreactor (ACM) device in order not to damage the integrity of the immobilized affinity ligands. Micro-valves 40 and 42 are then opened; micro-valve 114 is closed, and micro-valves 36, 38 and 118 remain closed. At this stage, a simple or complex sample containing one or more analytes of interest and/or their respective modified and/or altered corresponding counterpart is introduced through the inlet end of transport capillary 18 entirely to the outlet end of transport capillary 18, passing through analyte concentrator-microreactor (ACM) device 16. At this stage, all micro-valves are closed, including micro-valves 40 and 42, allowing for a closed microenvironment at analyte concentrator-microreactor (ACM) device 16, where temperature, motion of reagents, and time of incubation can be controlled to enhance the binding between the one or more analytes of interest and/or their respective modified and/or altered corresponding counterpart and the immobilized affinity ligands. Micro-valves 40 and 42 are then opened and a mild washing buffer is passed through transport passage 18 entirely to remove unwanted materials that may have been non-specifically bound to transport capillary 18 and inner area or channel 58 of analyte concentrator-microreactor (ACM) device 16, as shown in FIG. 6. Referring to FIG. 7, at this stage, micro-valves 40, 42 and 114 are closed and micro-valves 36, 38 and 118 are opened.

In step 110, referring to FIG. 7 of the experimental procedure, at inlet end 56 of separation capillary 22 mounted to cartridge-cassette 62 as shown on FIGS. 2 and 4, a plug of an elution buffer or solution is introduced, followed by separation buffer-1. The processes of introduction of a plug of elution buffer and separation are carried out by electro-migration principles, electro-osmotic flow, mechanical pressure, or a combination of electro-osmotic flow and mechanical pressure. A power supply-1 and/or a mechanical pump-1 are activated and used for introduction of a plug of an elution buffer or solution and for the separation process until the analytes of interest and/or their respective modified and/or altered corresponding counterpart reversible bound to the immobilized affinity ligands are released by the action of the elution buffer. Fiber optic 120 coupled to a detection system and positioned between analyte concentrator-microreactor (ACM) device 16 and micro-valve 118, can monitor the release of all bound analytes of interest and/or their respective modified and/or altered corresponding counterpart. At this stage, power supply-1 and mechanical pump-1 are deactivated and power supply-2 and mechanical pump-2 and/or mechanical pump 3 are activated. Micro-valves 36, 40, 42 and 118 are closed and micro-valves 114 and 38 are opened. The process of separation of the released analytes of interest and/or their respective modified and/or altered corresponding counterpart is carried out by electro-migration principles, electro-osmotic flow, mechanical pressure, or a combination of electro-osmotic flow and mechanical pressure, throughout separation capillary 22 entirely to outlet end 68, where separation capillary 22 is mounted to cartridge-cassette device 62 and one or more detectors are positioned on-line and/or off-line. The detectors can be in connection with the separation capillary through specially designed optic or interface devices, including fiber optics, wires, or the like, depending upon the principle of use. The detectors include ultraviolet, fluorescence, laser-induced fluorescence, infrared, mass spectrometers, nuclear-magnetic resonance, circular dichroism, electrochemical, amperometric, colorimetric, refractive index, conductimetric, diode array, radioactive and others. Derivatization of the analytes of interest and/or their respective modified and/or altered corresponding counterpart can be achieved by introducing a small amount of a chromophoric substance through inlet end of transport capillary 116 using mechanical pump-2 or through a separate and independent mechanical pump-3. Another method to incorporate a chromophoric substance is through inlet end 56 of separation capillary 22, when the chromophoric substance is a constituent of the elution buffer or solution, allowing the process of release and derivatization of the bound analytes of interest and/or their respective modified and/or altered corresponding counterpart to the immobilized ligands to occur simultaneously. Mechanical pumps 2 and 3 can also be used in alternate forms to introduce into the separation buffer one or two additives or viscous solutions to benefit the separation of one or more particular types of analytes of interest and/or their respective modified and/or altered corresponding counterpart. Mechanical pumps 2 and 3 connected to the auxiliary separation capillary or passage can function in coordination to generate a gradient of two buffers or solutions to also benefit the separation of one or more particular types of analytes of interest and/or their respective modified and/or altered corresponding counterpart. They can also function in coordination with a high-voltage power supply to improve selectivity of the separated analytes of interest and/or their respective modified and/or altered corresponding counterpart within the main separation capillary or passage.

Figure 8:
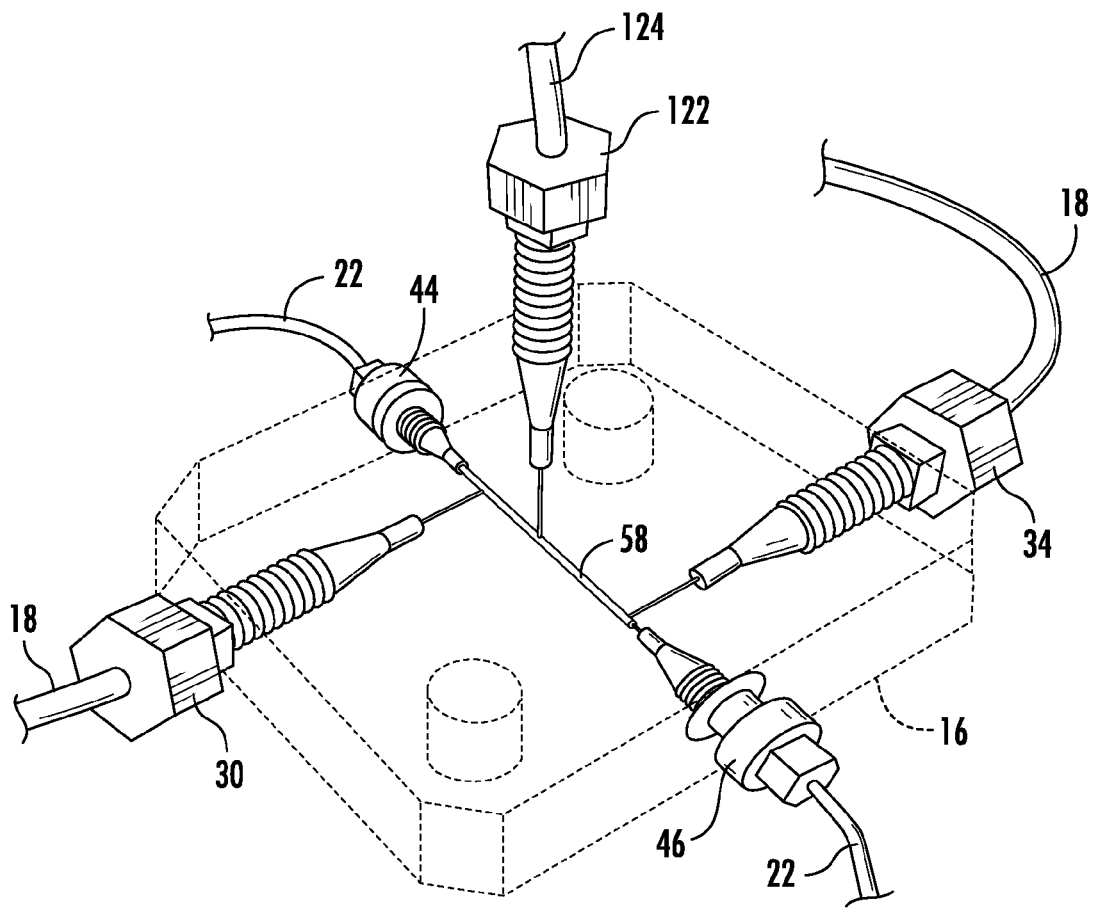
FIG. 8 illustrates a single analyte concentrator-microreactor (ACM) device having five entrance-exit ports identified as connection areas. Two are connecting areas to the analyte concentrator-microreactor (ACM) device with the transport capillary; two are connecting areas to analyte concentrator-microreactor (ACM) device with the separation capillary; and one is a connecting area to an auxiliary capillary. The auxiliary capillary allows the introduction or removal of microstructures to or from the internal channel of the analyte concentrator-microreactor (ACM) device.

FIG. 8 illustrates a single analyte concentrator-microreactor (ACM) device 16 having four entrance-exit ends or ports identified as inlet connection areas or inlet ends 30 and 44, and outlet connection areas or outlet ends 46 and 34. Two of the entrance-exit ends are connected to transport passage 18 and two are connected to separation passage 22. Transport capillary or passage is connected to analyte concentrator-microreactor (ACM) device 16 through inlet end 30 and outlet end 34. Separation capillary or passage 22 is connected to analyte concentrator-microreactor (ACM) device 16 through inlet end 44 and outlet end 46. A separate and independent port or entrance-exit end on the analyte concentrator-microreactor (ACM) device and connected through an auxiliary connector to an auxiliary capillary or passage is illustrated in FIG. 8. Auxiliary connector 122 is perpendicular positioned to analyte concentrator-microreactor (ACM) device 16 and making connection with internal area or channel 58 of analyte concentrator-microreactor (ACM) device 16, and to auxiliary capillary or passage 124. The function of the separate and independent port on the analyte concentrator-microreactor (ACM) device 16 and connected through the auxiliary connector 122 to an auxiliary capillary or passage 124 is to introduce to or remove from internal area or channel 58 of analyte concentrator-microreactor (ACM) device 16, a multitude of separated and independent microstructures such as beads, platelets, or chips, or integrated microstructures such as fibers, filaments, monolithic polymers, sol-gel or the like. The various microstructures provide support to affinity ligands, where they can be immobilized by physical interactions or through covalently chemical attachments and affinity capture selectively or non-selectively analytes of interest and/or their respective modified and/or altered corresponding counterpart present in simple or complex matrices. The introduction and removal of microstructures through the auxiliary capillary or passage to replace the existing ones after a single use or multiple uses is carried out by vacuum or pressure. The auxiliary capillary or passage is also used to provide new or replenish feeding media or fluids to the cells, subcellular structures or cellular receptors encapsulated within the analyte concentrator-microreactor (ACM) device. Keeping the cells, subcellular structures and/or cellular receptors alive will facilitate the metabolism or bioassay studies.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:
1. A portable and interchangeable box, comprising:
 a modular analyte concentrator-microreactor (ACM) device surrounded by four microvalves, each microvalve secured to an inside base of the box by support members, said box is mounted peripherally on a side wall or support platform of a capillary electrophoresis instrument or other analytical separation instrument through one or more fastening members;
 a transport capillary or passage connected to the analyte concentrator-microreactor (ACM) device;
 a separation capillary or passage connected to the analyte concentrator-microreactor (ACM) device;
 the analyte concentrator-microreactor (ACM) device having a first set of inlet and outlet ends connected to the transport capillary or passage;

the analyte concentrator-microreactor (ACM) device having a second set of inlet and outlet ends connected to the separation capillary or passage;

the analyte concentrator-microreactor (ACM) device having an internal passage or channel with a staggered configuration which includes an elongated concentration area;

the elongated concentration area of the analyte concentrator-microreactor (ACM) device serving as an intersection region where the transport capillary or passage and the separation capillary or passage connect at two separate and distant points;

the elongated concentration area of the analyte concentrator-microreactor (ACM) device providing a place of shelter for received microstructures or a matrix assembly;

one or more affinity ligands are immobilized to the microstructures or the matrix assembly localized within the elongated concentration area of the analyte concentrator-microreactor (ACM) device for generating a concentration space where concentration of one or more analytes of interest and/or their respective modified and/or altered corresponding molecular counterpart from a sample introduced into the transport capillary or passage occurs; and/or for generating a microreaction space where microreaction of the one or more analytes of interest and/or their respective modified and/or altered corresponding molecular counterpart from the sample introduced into the transport capillary or passage occurs;

alternatively the one or more affinity ligands are immobilized directly to an inner wall of a cavity or channel forming the elongated concentration area of the analyte concentrator-microreactor (ACM) device without the need of the microstructures or the matrix assembly; and controlling means for controlling flow of the sample or buffers in the transport capillary or passage and past the analyte concentrator-microreactor (ACM) device and conveyed by electromigration, electro-osmotic flow, mechanical pressure or a combination of electro-osmotic flow and mechanical pressure to an outlet end of the transport capillary or passage, and for controlling flow of buffers or solutions through the separation capillary or passage and past the analyte concentrator-microreactor (ACM) device and conveyed by electromigration, electro-osmotic flow, mechanical pressure or a combination of electro-osmotic flow and mechanical pressure to an outlet end of the separation capillary or passage;

wherein inlet and outlet ends of the separation capillary or passage connected to the analyte concentrator-microreactor (ACM) device are detachably connected by couplers to corresponding inlet and outlet ends of a separation capillary or passage of the capillary electrophoresis apparatus, the analytical separation instrument and/or a detector, creating an integrated unit;

wherein the integrated unit can capture, isolate, concentrate, allow microreactions, and separate released analytes of interest and/or their respective modified and/or altered corresponding molecular counterpart bound to and released from the analyte concentrator-microreactor (ACM) device by alternating fluid communication of a separation buffer supply and then an eluting buffer supply and delivering the released analytes of interest and/or their respective modified and/or altered corresponding molecular counterpart to the capillary electrophoresis instrument, analytical separation instrument and/or detector separately, independently and sequentially by electromigration, electro-osmotic flow, mechanical pressure or a combination of electro-osmotic flow and mechanical pressure within the separation capillary or passage.

2. The portable and interchangeable box of claim 1 wherein the microstructures or matrix assembly within the elongated concentration area of the analyte concentrator-microreactor (ACM) device have a surface or a wall having a surface to which the one or more affinity ligands are immobilized.

3. The portable and interchangeable box of claim 2 wherein the matrix assembly within the elongated concentration area of the analyte concentrator-microreactor (ACM) device includes a plurality of microstructures.

4. The portable and interchangeable box of claim 2 wherein the matrix assembly is free-floating, and retained within the elongated concentration area of the analyte concentrator-microreactor (ACM) device by pressure-resistant porous end walls or frits disposed at corresponding connecting points of the inlet and outlet ends of the analyte concentrator-microreactor (ACM) device and the transport capillary or passage and the separation capillary or passage.

5. The portable and interchangeable box of claim 2 wherein the matrix assembly within the elongated concentration area of the analyte concentrator-microreactor (ACM) device includes a fixed architecture defined by beaded microstructures interconnected to each other and to the inner wall of the cavity or channel forming the elongated concentration area of the analyte concentrator-microreactor (ACM) device.

6. The portable and interchangeable box of claim 2 wherein the matrix assembly within the elongated concentration area of the analyte concentrator-microreactor (ACM) device includes sol-gel or monoliths which are supports having a single, continuous piece of porous materials, nanoparticles and/or nanocomposites.

7. The portable and interchangeable box of claim 2 wherein the affinity ligands immobilized to the surface of the microstructures within the elongated concentration area of the analyte concentrator-microreactor (ACM) device or the surface of the inner wall of the cavity or channel forming the elongated concentration area of the analyte concentrator-microreactor (ACM) device are immobilized by physicochemical interactions or by covalent chemical interactions.

8. The portable and interchangeable box of claim 1 wherein the affinity ligands immobilized to the surface of the microstructures or the matrix assembly within the elongated concentration area of the analyte concentrator-microreactor (ACM) device or immobilized directly to the surface of the inner wall of the cavity or channel forming elongated concentration area of the analyte concentrator-microreactor (ACM) device include biological and non-biological affinity ligands, selected from intact antibodies, single-chain antibodies, antibody fragments, antigens, protein A, protein G, lectins, glycoproteins, glycolipids, enzymes, substrates, cofactors, coenzymes, drugs, vitamins, hormones, proteins, viruses, cells, subcellular structures, cell components, prions, receptors, membranes, dyes, metal-containing moieties, organometallic moieties, and synthetic ligands.

9. The portable and interchangeable box of claim 1 wherein the analytes of interest and/or their respective modified and/or altered corresponding molecular counterpart to be captured, isolated and concentrated from simple or complex matrices, include biological and non-biological analytes selected from the group consisting of intact antibodies, antibody fragments, antigens, protein A, protein G, lectins, glycoproteins, glycolipids, enzymes, substrates, cofactors, coenzymes, drugs, vitamins, hormones, proteins, viruses, cells, subcellular structures, cell components, prions, receptors, membranes, dyes, metal-containing moieties, organometallic moieties, and synthetic ligands.

10. The portable and interchangeable box of claim 1 wherein the at least one or more affinity ligands immobilized to the surface of the microstructures or matrix assembly within the elongated concentration area of the analyte concentrator-microreactor (ACM) device or immobilized directly to the surface of the inner wall of the cavity or channel forming the elongated concentration area of the analyte concentrator-microreactor (ACM) device is capable of performing a reversible affinity capture reaction with the one or more analytes of interest and/or their respective modified and/or altered corresponding molecular counterpart present in the sample.

11. The portable and interchangeable box of claim 1 wherein at least one or more affinity ligands immobilized to the surface of the microstructures or matrix assembly retained within the elongated concentration area of the analyte concentrator-microreactor ACM device or immobilized directly to the surface of the inner wall of the cavity or channel forming forms the elongated concentration area of the analyte concentrator-microreactor (ACM) device is capable of performing one chemical or biochemical reaction with the one or more analytes of interest and/or their respective modified and/or altered corresponding molecular counterpart present in the sample.

12. The portable and interchangeable box of claim 11 wherein the at least one chemical or biochemical reaction carried out within the cavity or channel forming the elongated concentration area of the analyte concentrator-microreactor (ACM) device includes peptide synthesis, nucleic acid synthesis, or an enzymatic reaction.

13. The portable and interchangeable box of claim 1 wherein the elongated concentration area of the analyte concentrator-microreactor (ACM) device has encapsulated cellular and/or subcellular structures localized and retained therein.

14. The portable and interchangeable box of claim 13 wherein the encapsulated cellular or subcellular structures localized and retained within the elongated concentration area of the analyte concentrator-microreactor (ACM) device are adapted to perform metabolic studies.

15. The portable and interchangeable box of claim 1 wherein the elongated concentration area of the analyte concentrator-microreactor (ACM) device has an encapsulated cellular receptor localized and retained therein.

16. The portable and interchangeable box of claim 15 wherein the encapsulated cellular receptor localized and retained within the elongated concentration area of the analyte concentrator-microreactor (ACM) device is adapted to perform bioactivity studies.

17. The portable and interchangeable box of claim 1 wherein the analyte concentrator-microreactor (ACM) device has an acoustic micromixing system.

18. The portable and interchangeable box of claim 1 wherein the analyte concentrator-microreactor (ACM) device has a microwave pulse system.

19. The portable and interchangeable box of claim 1 wherein the analyte concentrator-microreactor (ACM) device has a temperature control system.

20. The portable and interchangeable box of claim 1 wherein the analyte concentrator-microreactor (ACM) device has connecting points to the transport capillary or passage and separation capillary or passage that are hermetically sealed.

21. The portable and interchangeable box of claim 1 wherein the micro-valves are operated manually or by electronic-controlled circuitry.

22. The portable and interchangeable box of claim 20 wherein the controlling means controls the operation of a cleaning buffer fluid means for introducing a cleaning buffer, optimization buffer fluid means for introducing an optimization buffer, sample fluid means for introducing the sample, and washing buffer fluid means for introducing a washing buffer fluid through the transport capillary or passage.

23. The portable and interchangeable box of claim 22 wherein the controlling means controls a separation buffer fluid means for introducing a separation buffer fluid, and a plug of elution buffer fluid means for introducing a plug of elution buffer followed by the separation buffer fluid introduced through the separation capillary or passage.

24. The portable and interchangeable box of claim 1 wherein the portable and interchangeable box and/or the modular analyte concentrator-microreactor (ACM) device are color coded to identify the one or more specific affinity ligands,
wherein the modular analyte concentrator-microreactor (ACM) device is used for the determination of one or more analyte biomarkers associated with the diagnosis and/or prognosis of a particular disease or toxic state, and/or to identify the normality-abnormality of a certain organ, tissue, cluster cells, or circulating cell operation and/or application.

25. The portable and interchangeable box of claim 1 wherein the operation of the portable and interchangeable box, containing the modular analyte concentrator-microreactor (ACM) device, when connected to the capillary electrophoresis apparatus, the analytical separation instrument, and/or the detector is carried out in a coordinated fashion through an electronically-controlled circuitry of the integrated unit.

26. The portable and interchangeable box of claim 1 wherein the modular analyte concentrator-microreactor (ACM) device has a separate and independent port connected through an auxiliary connector to an auxiliary capillary or passage where the microstructures with immobilized affinity ligands are introduced and/or replaced to and from the internal passage or channel of the analyte concentrator-microreactor (ACM) device after a single use or multiple uses.

27. The portable and interchangeable box of claim 1 wherein the modular analyte concentrator-microreactor (ACM) device has an auxiliary port or passage connected to an auxiliary capillary or passage used to provide and/or replenish feeding media fluids for maintaining alive encapsulated cells, subcellular structures, and/or cellular receptors.

28. The portable and interchangeable box of claim 1 wherein the capillary electrophoresis instrument or other analytical separation instrument to which the portable and interchangeable box is connected to form the integrated unit is a microchip-microfluidic format of the capillary electrophoresis instrument, a high-performance liquid chromatography instrument, a low-pressure liquid-chromatography instrument, a ultra-pressure high-performance liquid chromatography instrument, a nano high-performance liquid chromatography instrument, a gas chromatography instrument, or a modified version of these instruments.

29. The portable and interchangeable box of claim 27 wherein the integrated unit formed utilizes one or more detectors of on-line and/or off-line detector types, including ultraviolet, fluorescence, laser-induced fluorescence, mass spectrometer, nuclear magnetic resonance, circular dichroism, electrochemical, conductivity, radioactive and/or modified versions of these detectors.

30. The integrated unit of claim 28 wherein the separation capillary or passage is filled with an electrically conductive fluid that is used for separation of the captured, isolated and released analytes of interest, and also preserves the integrity of the immobilized affinity ligands.

31. The integrated unit of claim 28 wherein the separation capillary or passage is filled with a gel matrix containing an electrically conductive fluid that is used for separation of the captured, isolated and released analytes of interest, and also preserves the integrity of the immobilized affinity ligands.

32. The integrated unit of claim 23 wherein the plug of elution buffer contains an organic solvent, a chaotropic agent, a high salt buffer, a low pH buffer, a high pH buffer, a detergent, or a combination of them and/or a chromophoric substance.

33. A portable and interchangeable box, comprising:
one or more modular analyte concentrator-microreactor (ACM) devices, each of the analyte concentrator-microreactor (ACM) devices being surrounded by four microvalves, each microvalve secured to an inside base of the box by support members, said portable and interchangeable box is mounted peripherally on a side wall or support platform of a capillary electrophoresis instrument or other analytical separation instrument through one or more fastening members;
a transport capillary or passage connected separately and independently to each analyte concentrator-microreactor (ACM) device;
a separation capillary or passage connected to the one or more analyte concentrator-microreactor (ACM) devices;
each of the one or more analyte concentrator-microreactor (ACM) devices having a first set of inlet and outlet ends connected separately and independently to each transport capillary or passage;
each of the one or more analyte concentrator-microreactor (ACM) devices having a second set of inlet and outlet ends connected separately and independently to the separation capillary or passage;
each of the one or more analyte concentrator-microreactor (ACM) devices having an internal passage or channel with a staggered configuration which includes an elongated microreaction or concentration area;
each elongated microreaction or concentration area of the analyte concentrator-microreactor (ACM) device serving as an intersection region where each transport capillary or passage and the separation capillary or passage connect separately and independently at two separate and distant points;
each elongated microreaction or concentration area of the analyte concentrator-microreactor (ACM) device providing a place of shelter for received microstructures or a matrix assembly;
one or more affinity ligands are immobilized to the microstructures or the matrix assembly localized within the elongated microreaction or concentration area of a first of the one or more analyte concentrator-microreactor (ACM) devices for generating a microreaction space where microreaction of one or more analytes of interest and/or their respective modified and/or altered corresponding counterpart from a sample introduced into the transport capillary or passage occurs and/or
for generating a concentration space where concentration of the one or more analytes of interest and/or their respective modified and/or altered corresponding counterpart generated in the first analyte concentrator-microreactor (ACM) device occurs;
alternatively the one or more affinity ligands are immobilized directly, separately and independently to an inner wall of cavities or channels forming the elongated microreaction or concentration area of each analyte concentrator-microreactor (ACM) device without the need of the microstructures or matrix assembly; and
controlling means for controlling flow of the sample and/or buffers in each of the transport capillaries or passages and past each of the analyte concentrator-microreactor (ACM) devices, and for controlling flow of buffers or solutions through the separation capillary or passage and past each of the analyte concentrator-microreactor (ACM) devices and conveyed by electromigration, electro-osmotic flow, mechanical pressure or a combination of electro-osmotic flow and mechanical pressure;
inlet and outlet ends of the separation capillary or passage connected to each of the analyte concentrator-microreactor (ACM) devices are detachably connected by couplers to corresponding inlet and outlet ends of a separation capillary or passage of the capillary electrophoresis apparatus, the analytical separation instrument and/or a detector, creating an integrated unit.

34. The portable and interchangeable box of claim 33 wherein each of the elongated microreaction or concentration areas includes a matrix assembly disposed therein having a surface or a wall having a surface to which one or more affinity ligands are immobilized.

35. The portable and interchangeable box of claim 33 wherein the matrix assembly within the elongated microreaction or concentration area of the analyte concentrator-microreactor (ACM) device includes a plurality of microstructures.

36. The portable and interchangeable box of claim 33 wherein the matrix assembly within the elongated microreaction or concentration area of the analyte concentrator-microreactor (ACM) device is free-floating, and each of the elongated microreaction or concentration areas retains the free-floating matrix assembly by pressure-resistant porous end walls or frits disposed at corresponding connecting points of the inlet and outlet ends of each of the analyte concentrator-microreactor (ACM) devices and each of the transport capillaries or passages and the separation capillary or passage.

37. The portable and interchangeable box of claim 33 wherein the matrix assembly within the elongated microreaction or concentration area of the analyte concentrator-microreactor (ACM) device includes a fixed architecture defined by beaded microstructures interconnected to each other and to the inner wall of the cavity or channel forming the elongated microreaction or concentration area of each of the analyte concentrator-microreactor (ACM) devices.

38. The portable and interchangeable box of claim 33 wherein within the elongated microreaction or concentration area of the analyte concentrator-microreactor (ACM) device the matrix assembly includes sol-gel or monoliths which are supports having a single, continuous piece of porous materials, nanoparticles and/or nanocomposites.

39. The portable and interchangeable box of claim 33 wherein the affinity ligands immobilized to the surface of the microstructures within the elongated microreaction or concentration area of the analyte concentrator-microreactor (ACM) device or surface of the inner wall of the cavity or channel forming the elongated microreaction or concentration area of each of the analyte concentrator-microreactor (ACM) devices are immobilized by physicochemical interactions or by covalent chemical interactions.

40. The portable and interchangeable box of claim 33 containing two of the modular analyte concentrator-microreactor (ACM) devices each having the elongated microreaction or concentration area, wherein the affinity ligands immobilized to the surface of the microstructures or surface of the inner wall of the cavity or channel forming the elongated microreaction or concentration area of the first analyte concentrator-microreactor (ACM) device include one or more proteolytic enzymes with the purpose to cleave proteins into smaller peptide units.

41. The portable and interchangeable box of claim 33 containing two of the modular analyte concentrator-microreactor (ACM) devices each having each the elongated concentration-microreaction or concentration area, wherein the affinity ligands immobilized to the surface of the microstructures or the surface of the inner wall of the cavity or channel forming the elongated microreaction or concentration area of the first analyte concentrator-microreactor (ACM) device include one or more nuclease enzymes with the purpose to cleave larger nucleic acids components, of deoxyribonucleic acid (DNA) or ribonucleic acid (RNA), into smaller nucleic acid units.

42. The portable and interchangeable box of claim 33 containing two of the modular analyte concentrator-microreactor (ACM) devices each having each the elongated concentration-microreaction or concentration area, wherein the affinity ligands immobilized to the surface of the microstructures or the surface of the inner wall of the cavity or channel forming the elongated microreaction or concentration area of the second analyte concentrator-microreactor (ACM) device include one or more affinity ligands selected from the group consisting of intact antibodies, single-chain antibodies, antibody fragments, lectins and metal-capturing compounds to affinity capture one or more peptides generated by the action of proteases in the first analyte concentrator-microreactor (ACM) device.

43. The portable and interchangeable box of claim 41 wherein the affinity ligands immobilized to the surface of the microstructures or surface of the inner wall of the cavity or channel forming the elongated microreaction or concentration area of the second analyte concentrator-microreactor (ACM) device include preferentially one or more affinity ligands selected from the group consisting of single-chain antibodies, antibody fragments, and hybridization capture probes to affinity capture nucleic acids generated by the action of nucleases in the first analyte concentrator-microreactor (ACM) device.

44. The portable and interchangeable box of claim 33 wherein the couplers are positioned peripherally on the side wall or platform of the capillary electrophoresis apparatus or the analytical separation instrument.

45. The portable and interchangeable box of claim 33 wherein the separation capillary or passage of the capillary electrophoresis apparatus or the analytical separation is mounted and secured to a cartridge-cassette unit.

46. The portable and interchangeable box of claim 33 wherein a protein containing sample is introduced through a first analyte concentrator-microreactor (ACM) device where one or more proteolytic enzymes are immobilized, a digestion time is allowed and a process of separation is performed to separate generated peptides passing through a second analyte concentrator-microreactor (ACM) device until reaching an analyte detector means; the second analyte concentrator-microreactor (ACM) device containing one or more affinity ligands selected from the group consisting of intact antibody, single-chain antibody, antibody fragment and lectin to capture the peptides that have affinity for the one or more affinity ligands, and an elution process is allowed to release and separate the bound peptides until reaching the analyte detector means.

47. The portable and interchangeable box of claim 1, connected to the detector, wherein the detector is a mass spectrometer.

48. A portable and interchangeable box, comprising:
a modular analyte concentrator-microreactor (ACM) device surrounded by four microvalves, each microvalve secured to an inside base of the box by support members, said portable and interchangeable box is mounted peripherally on a side wall or support platform of a capillary electrophoresis instrument or other analytical separation instrument through one or more fastening members;
a transport capillary or passage connected to the analyte concentrator-microreactor (ACM) device;
a main separation capillary or passage connected to the analyte concentrator-microreactor (ACM) device;
the analyte concentrator-microreactor (ACM) device having a first set of inlet and outlet ends connected to the transport capillary or passage;
the analyte concentrator-microreactor (ACM) device having a second set of inlet and outlet ends connected to the main separation capillary or passage;
the analyte concentrator-microreactor (ACM) device having an internal passage or channel with a staggered configuration which includes an elongated concentration area;
the elongated concentration area of the analyte concentrator-microreactor (ACM) device serving as an intersection region where the transport capillary or passage and the main separation capillary or passage connect at two separate and distant points;
the elongated concentration area of the analyte concentrator-microreactor (ACM) device providing a place of shelter for received microstructures or a matrix assembly;
one or more affinity ligands are immobilized to the microstructures or the matrix assembly localized within the elongated concentration area of the analyte concentrator-microreactor (ACM) device for generating a concentration space where concentration of one or more analytes of interest and/or their respective modified and/or altered corresponding molecular counterpart from a sample introduced into the transport capillary or passage occurs and/or
for generating a microreaction space where microreaction of the one or more analytes of interest and/or their respective modified and/or altered corresponding molecular counterpart from the sample introduced into the transport capillary or passage occurs;
alternatively the one or more affinity ligands are immobilized directly to the inner wall of a cavity or channel forming the elongated concentration area of the analyte concentrator-microreactor (ACM) device without the need of the microstructures or the matrix assembly; and
controlling means for controlling flow of the sample or buffers in the transport capillary or passage and past the analyte concentrator-microreactor (ACM) device and conveyed by electromigration, electro-osmotic flow, mechanical pressure or a combination of electro-osmotic flow and mechanical pressure to an outlet end of the transport capillary or passage, and for controlling flow of buffers or solutions through the main separation capillary or passage and past the analyte concentrator-microreactor (ACM) device and conveyed by electromigration, electro-osmotic flow, mechanical pressure or a combination of electro-osmotic flow and mechanical pressure to an outlet end of the main separation capillary or passage;

inlet and outlet ends of the main separation capillary or passage connected to the analyte concentrator-microreactor (ACM) device are detachably connected by couplers to corresponding inlet and outlet ends of a separation capillary or passage of the capillary electrophoresis apparatus, the analytical separation instrument and/or a detector, creating an integrated unit;

wherein the integrated unit can capture, isolate, concentrate, allow microreactions, and separate released analytes of interest and/or their respective modified and/or altered corresponding molecular counterpart bound to and released from the analyte concentrator-microreactor (ACM) device by alternating fluid communication of a separation buffer supply and then an eluting buffer supply and delivering the released analytes of interest and/or their respective modified and/or altered corresponding molecular counterpart to the capillary electrophoresis instrument, analytical separation instrument and/or detector separately, independently, and sequentially by electromigration, electro-osmotic flow, mechanical pressure or a combination of electro-osmotic flow and mechanical pressure within the main separation capillary or passage;

an auxiliary separation capillary or passage connected by a T-coupler to the main separation capillary or passage localized downstream of the analyte concentrator-microreactor (ACM) device to introduce cleaning buffers and separation buffer from an inlet end of the auxiliary separation capillary or passage to the outlet end of the main separation capillary or passage;

an auxiliary controlling means for controlling flow of separation buffer in the auxiliary separation capillary or passage downstream of the analyte concentrator-microreactor (ACM) device and conveyed by electromigration, electro-osmotic flow, mechanical pressure or a combination of electro-osmotic flow and mechanical pressure to the outlet end of the main separation capillary or passage, and operatively in coordination with the controlling means, which is localized in the main separation capillary or passage upstream of the T-coupler.

49. The portable and interchangeable box of claim 48 wherein an auxiliary detection means is placed in contact with the main separation capillary or passage downstream of the analyte concentrator-microreactor (ACM) device and upstream of the controlling means localized in the main separation capillary or passage.

50. The portable and interchangeable box of claim 48 wherein a first power supply and a first mechanical pump are positioned at the inlet end of the main separation capillary or passage and a second power supply and a second mechanical pump are positioned at the inlet end of the auxiliary separation capillary or passage.

51. The portable and interchangeable box of claim 48 wherein the separation buffer is introduced from the inlet end of the auxiliary separation capillary or passage to an analyte detection means and contains additives including detergents, organic acids, chaotropic agents, cyclodextrins and/or substances that can enhance the selectivity separation of the analytes of interest and/or their respective modified and/or altered corresponding molecular counterpart and damage the integrity of the affinity ligands immobilized to the analyte concentrator-microreactor (ACM) device.

52. The portable and interchangeable box of claim 48 wherein a first power supply and a first mechanical pump positioned at the inlet end of the main separation capillary or passage operate separately or simultaneously to introduce a first separation buffer that preserves the integrity of the affinity ligands immobilized to the analyte concentrator-microreactor (ACM) device followed by a plug of an elution buffer or solution, and a second power supply and one or more second mechanical pumps that operate separately or simultaneously and in coordination are positioned at the inlet end of the auxiliary separation capillary or passage to introduce a second separation buffer, wherein the means for controlling flow of the first separation buffer in the main separation capillary or passage comprises first and second microvalves of the four microvalves located at the second set of inlet and outlet ends of the analyte concentrator-microreactor (ACM) device, and a third valve for controlling flow of second separation buffer in the auxiliary separation capillary or passage is located at the inlet end of the auxiliary separation capillary or passage downstream of the analyte concentrator-microreactor (ACM) device, wherein said first and second microvalves are opened and said third valve is closed for introducing said first separation buffer, thereafter the first and second microvalves are closed and the third valve is opened for introducing said second separation buffer, thereafter the first and second microvalves are opened and the third valve is closed for introducing the plug of the elution buffer or solution to release bound analytes from the analyte concentrator-microreactor (ACM) device and thereafter once the bound analytes are released the first and second microvalves are closed and the third valve is opened, wherein the second separation buffer is localized away from the analyte concentrator-microreactor (ACM) device, in order to avoid constituents of the second separation buffer to damage the integrity of the affinity ligands immobilized to the analyte concentrator-microreactor (ACM) device and the second separation buffer is used to improve the separation of the released analytes of interest and/or their respective modified and/or altered corresponding molecular counterpart that have passed an auxiliary detection means through the main separation capillary or passage toward an analyte detection means localized at the capillary electrophoresis apparatus.

53. The portable and interchangeable box of claim 52 wherein the first and second mechanical pumps can function in coordination with each other or in coordination with the first and/or second power supply to generate a gradient of two buffers or solutions to improve selectivity benefiting the separation of one or more particular types of analytes of interest and/or their respective modified and/or altered corresponding molecular counterpart separated within the main separation capillary or passage.

54. The portable and interchangeable box of claim 1 wherein the portable and interchangeable box and/or the analyte concentrator-microreactor (ACM) device are color-coded to represent the presence of the specific affinity ligands and/or a particular functionality, wherein the analyte concentrator-microreactor (ACM) device is used for the determination of a certain number of analyte biomarkers associated to the diagnosis and/or prognosis of a particular disease or toxic state, and/or to identify the normality-abnormality of a certain organ, tissue, cluster cells, or circulating cell.

55. The portable and interchangeable box of claim 1 wherein the separation is carried out by one or more of any of the modes of capillary electrophoresis.

56. The portable and interchangeable box of claim 1 wherein the controlling means comprises a valve system operatively associated with the transport capillary or passage and the separation capillary or passage for independently controlling the flow of the sample in the transport capillary or passage and separately and independently forming a microenvironment in the elongated concentration area of the analyte concentrator-microreactor (ACM) device to mix reagents to optimize the binding and capture of the one or more analytes of interest and/or their respective modified and/or altered corresponding molecular counterpart.

57. The portable and interchangeable box of claim 56 wherein the valve system includes valves which are operated by electronically controlled circuitry.

58. The portable and interchangeable box of claim 56 wherein the valve system includes valves which are manually operated.

* * * * *